(12) United States Patent
Miyamoto et al.

(10) Patent No.: US 8,969,319 B2
(45) Date of Patent: Mar. 3, 2015

(54) AGENT FOR APPLYING TO MUCOSA AND METHOD FOR THE PRODUCTION THEREOF

(75) Inventors: Kenji Miyamoto, Tokyo (JP); Katsuya Takahishi, Tokyo (JP); Yuuji Shimojima, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 13/070,210

(22) Filed: Mar. 23, 2011

(65) Prior Publication Data

US 2011/0207695 A1 Aug. 25, 2011

Related U.S. Application Data

(63) Continuation of application No. 12/083,189, filed as application No. PCT/JP2006/320801 on Oct. 12, 2006, now abandoned.

(30) Foreign Application Priority Data

Oct. 12, 2005 (JP) ................................. 2005-297170
Jun. 9, 2006 (JP) ................................. 2006-160478

(51) Int. Cl.
*A01N 43/04* (2006.01)
*A61K 31/715* (2006.01)
*A61K 31/727* (2006.01)
*A61K 47/48* (2006.01)
*A61K 9/00* (2006.01)
*A61K 31/726* (2006.01)
*A61K 31/728* (2006.01)
*A61K 49/00* (2006.01)

(52) U.S. Cl.
CPC ........... *A61K 47/4823* (2013.01); *A61K 9/0048* (2013.01); *A61K 9/006* (2013.01); *A61K 31/726* (2013.01); *A61K 31/728* (2013.01); *A61K 49/0043* (2013.01); *A61K 49/0054* (2013.01); *A61K 9/0034* (2013.01)
USPC .............................................. 514/54; 514/56

(58) Field of Classification Search
CPC ... A61K 9/0048; A61K 9/006; A61K 31/728; A61K 31/726
See application file for complete search history.

(56) References Cited

U.S. PATENT DOCUMENTS

| 5,462,976 | A | 10/1995 | Matsuda et al. |
| 5,733,892 | A | 3/1998 | Sakurai et al. |
| 6,025,444 | A | 2/2000 | Waki et al. |
| 6,031,017 | A | 2/2000 | Waki et al. |
| 6,602,859 | B2 | 8/2003 | Miyamoto et al. |
| 2001/0044423 | A1 | 11/2001 | Takahashi et al. |

FOREIGN PATENT DOCUMENTS

| CN | 1207744 A | 2/1999 |
| EP | 0713859 | 5/1996 |
| EP | 0891775 | 1/1999 |
| JP | 62-064802 | 3/1987 |
| JP | 1-238530 | 9/1989 |
| JP | HEI-1-238530 | 9/1989 |
| JP | 06073102 A | 3/1994 |
| JP | HEI-8-143604 | 4/1996 |
| JP | 10-226704 | 8/1998 |
| JP | 11-071282 | 3/1999 |
| JP | 2001-316284 | 11/2001 |
| JP | 2002-037746 | 2/2002 |
| JP | 2002-356447 | 12/2002 |
| WO | WO 98/29125 | 7/1998 |
| WO | WO 00/01733 | 1/2000 |
| WO | WO 00/56344 | 9/2000 |
| WO | 2006030965 | 3/2006 |

OTHER PUBLICATIONS

Definition of "prevention" from the Institute for International Medical Education [online], [Retrieved on Mar. 24, 2011]. Retrieved from the internet <http://www.iime.org/glossary.htm>. Published Feb. 2002, p. 1, 2, 26, 27 and 39.*
Definition of "prevent" from the Merriam Webster Online Dictionary [online]m [Retrieved on Aug. 15, 2008], <http://www.merriam-webster.com/cgi-bin/dictionary?book=Dictionary&va=prevent>.
"Symptoms and diagnosis of eye disorders," Merck Manual Home Edition [online], [retrieved Oct. 27, 2010], <http://web.archive.org/web/20060321050841/www.merck.com/mmhe/print/sec20/ch225/ch225b.html>.
"Cataract," Merck Manual Second Home Edition [online], [retrieved Oct. 27, 2010]. <http://web.archive.org/web/20051101072954/www.merck.com/mmhe/print/sec20/ch231/ch231a.html> Published Aug. 7, 2005.l.
"Your Cornea: Conditions, Symptoms and Treatments," MedicineNet.com [online], [retrieved Mar. 10, 2011], <http;//www.medicinenet.com/script/main/art.asp?articlekey=43321&pf=3&page=1>.
European Search Report related to EP 06811990.8.
International Search Report related to PCT/JP 2006/320801.
International Preliminary Report on Patentability related to PCT/JP2006/320801.
Chinese Office Action dated Jan. 29, 2010 for related patent application No. CN200680038019.9 and translation.
Chinese Office Action dated Nov. 16, 2011 for related patent application No. CN200680038019.9 and translation.
European Office Action dated Jan. 9, 2012 for related patent application No. EP06811990.8.

(Continued)

*Primary Examiner* — Scarlett Goon
(74) *Attorney, Agent, or Firm* — Oblon, Spivak, McClelland, Maier & Neustadt, L.L.P.

(57) ABSTRACT

An agent for applying to mucosa capable of persistently exerting a therapeutic effect on disorders such as inflammation and lesions in the mucosa even by a lower frequency of administration because the agent can stay at a diseased site for a long period of time by exhibiting a high staying property in a mucosal epithelial layer is provided, said agent for application to mucosa containing glycosaminoglycan (GAG) into which a hydrophobic group is introduced via a binding chain, as an active ingredient.

4 Claims, 20 Drawing Sheets

(56) References Cited

OTHER PUBLICATIONS

Usui et al., Treatment of Corneal Epithelial Lesions by Ropical Sodium Hyaluronate, Japanese Review of Clinical Ophthalmology, 1993, vol. 87, No. 4, p. 730-733.
Notification of Reasons for Rejection for related Japanese Patent App. No. JP 2012-144630, dated Oct. 17, 2013.
Suemaru et al., Efficacy of Hyaluronic Acid for Corneal Wound Healing after Excimer Laser Keratectomy: Histological Observations, Folia Ophthalmology Japonica, 1996, vol. 47, p. 1446-9.
Usui et al., Tips on Diagnosis and Treatment of Corneal Diseases, Ophthalmology 2005, 47: 1169-1176.
Nakamura et al., Hyaluronan Stimulates Epithelial Wound Healing in the Rabbit Cornea, Folia Ophthalmologica Japonica, 1995, vol. 46, p. 1256-60.
Chinese Office Action for related CN App. No. 201210562380.9 dated Nov. 8, 2013, incorrectly stated to be a Japanese Office Action in the IDS submitted on Feb. 7, 2014.
C. Ekmekcioglu et al., Cancer Letters, vol. 128, pp. 137-144 (1998).
H.S. Dua, et al., British Journal of Ophthalmology, vol. 78, pp. 401-408 (1994).

* cited by examiner

Healing rate (cm²/day, n=42(n=14 × 3 times), Mean ± SD, *. P<0.05)

Healed area (N=8, * : P<0.05, ▲ : P<0.0556)

Healing rate (n=24 ( n=8×3 times), Mean±SD, * P<0.05)

a. 0.3% solution of fluorescence labeled HA

FA images: excitation wavelength; 495 nm, absorption wavelength; 460 nm b.

b 0.3% solution of fluorescence labeled
cinnamate derivative-introduced HA
30 minutes after administration FA images: excitation wavelength: 495 nm, absorption wavelength: 460 nm c. 0.3% solution of fluorescence labeled HA FA images: excitation wavelength: 495 nm, absorption wavelength: 460 nm d.

d. 0.3% solution of fluorescence labeled
cinnamate derivative-introduced HA
1 hour after administration FA images: excitation wavelength; 495 nm, absorption wavelength; 460 nm a. 0.3% solution of fluorescence labeled HA FA images: excitation wavelength: 495 nm, absorption wavelength: 460 nm b.

b. 0.3% solution of fluorescence labeled
cinnamate derivative-introduced HA
1.5 hours after administration FA images: excitation wavelength: 495 nm, absorption wavelength: 460 nm c. 0.3% solution of fluorescence labeled HA FA images: excitation wavelength: 495 nm, absorption wavelength: 460 nm d. 0.3% solution of fluorescence labeled
cinnamate derivative-introduced HA
2.5 hours after administration FA images: excitation wavelength; 495 nm, absorption wavelength; 460 nm 0.3 % HA solution 0.3 % solution of cinnamate derivative-introduced HA Moisturizing effect in removed cornea Test results

**: P<0.01

AGENT FOR APPLYING TO MUCOSA AND METHOD FOR THE PRODUCTION THEREOF

CROSS REFERENCES TO RELATED APPLICATIONS

This application is a Continuation Application of U.S. patent application Ser. No. 12/083,189, filed on Apr. 4, 2008, now abandoned which was a 371 of International Patent Application No. PCT/JP2006/320801, filed on Oct. 12, 2006, and claims priority to Japanese Patent Application No. 2005-297170, filed on Oct. 12 2005, and Japanese Patent Application No. 2006-160478, filed on Jun. 9, 2006.

TECHNICAL FIELD

The present invention relates to an agent for applying to mucosa containing a hydrophobic group binding type glycosaminoglycan as an active ingredient, and a method for production thereof.

BACKGROUND ART

Conventionally, as substances having healing effects on mucosal disorders such as inflammation and lesions, hyaluronic acid which is a representative glycosaminoglycan (hereinafter described as "GAG") has been known (e.g., Patent Document 1). However, in mucosa in the cornea, oral cavity and nasal cavity, and conjunctiva which contacts with the external world, and mucosa in the urinary bladder, the mucosal surfaces are washed with secretions and excretions such as tear fluid, salivary fluid and urine, and foreign substances are removed. Thus derivatives of GAG which keep medicinal effects inherent in GAG and exert a high staying property in these mucosal tissues have been demanded.

Meanwhile, photoreactive hyaluronic acid whose water-solubility has been increased by binding a photocrosslinking group such as cinnamic acid to hyaluronic acid and further giving an alkali treatment thereto has been known (e.g., Patent Document 2). This photoreactive hyaluronic acid has been provided by binding a photocrosslinking group such as cinnamic acid to hyaluronic acid in order to provide medical materials such as anti-adhesion materials by giving the photocrosslinking, and does not aim at enhancing the staying property in the mucosal tissue.

[Patent Document 1] Japanese Published Unexamined Patent Publication No. Hei-1-238530
[Patent Document 2] Japanese Published Unexamined Patent Publication No. 2002-249501

DISCLOSURE OF THE INVENTION

Problem to be Solved by the Invention

The present invention aims at providing an agent for applying to mucosa, which exerts an excellent staying property and pharmacological effects in mucosa.

Means for Solving the Problem

As a result of an extensive study for solving the above problem, the present inventors have found that "hydrophobic group binding type GAG" obtained by binding a hydrophobic group to GAG via a binding chain can be used as an extremely excellent active ingredient in an agent for applying to mucosa because this GAG keeps healing effects inherent in GAG on mucosal disorders such as inflammation and lesions and exhibits a high staying property when applied thereto, and have completed the present invention.

The present invention relates to an agent for applying to mucosa which contains glycosaminoglycan (GAG) into which the hydrophobic group is introduced via the binding chain.

Effects of the Invention

The agent for applying to mucosa of the present invention can exert the persistent healing effect on the mucosal disorder such as inflammation and lesions even by low frequent administration because this can stay at a diseased site for a long period of time by exhibiting high staying property in the mucosa.

BEST MODES FOR CARRYING OUT THE INVENTION

Figure 1:
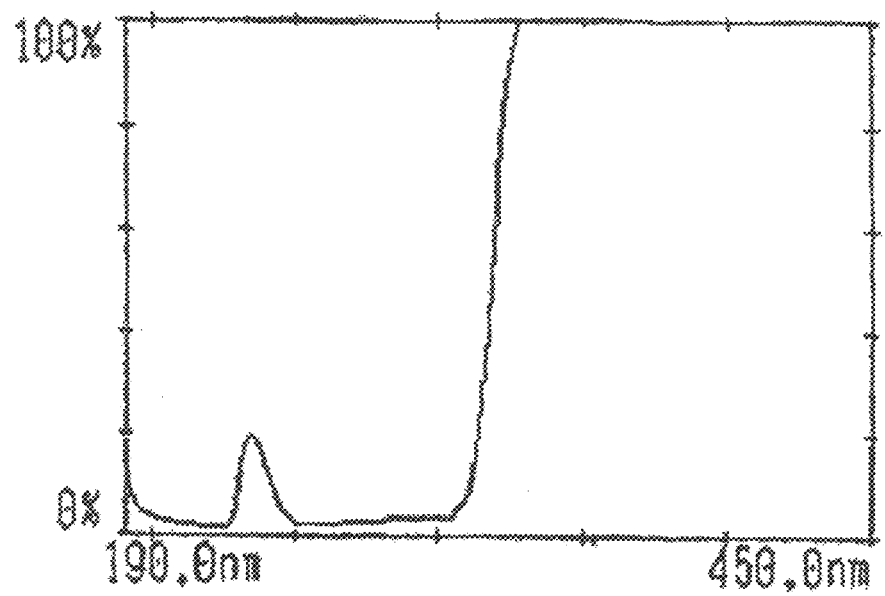
FIG. 1 is a view showing a spectrum of light transmittance.

The present invention will be described in more detail below by the best modes for carrying out the invention.

Herein, an alkyl group refers to a straight or branched aliphatic hydrocarbon group having. a described number of carbon atoms. An alkenyl group refers to a straight or branched aliphatic hydrocarbon group having a described number of carbon atoms, having at least one double bond. An alkynyl group refers to a straight or branched aliphatic hydrocarbon group having a described number of carbon atoms, having at least one triple bond.

An aryl group refers to a monocyclic or polycyclic aromatic hydrocarbon group having 6 to 20 carbon atoms as ring-constituting atoms. A heteroaryl group refers to a monocyclic or polycyclic aromatic hydrocarbon group having 3 to 20 carbon atoms and one or heteroatoms selected from nitrogen, sulfur and oxygen atoms as the ring-constituting atoms.

An arylalkyl group refers to the alkyl group defined above substituted with the aryl group defined above. An arylalkynyl group refers to the alkenyl group defined above substituted with the aryl defined above. An arylalkynyl group is the alkynyl group defined above substituted with the aryl group defined above.

An amino acid group refers to a group derived by losing a carboxyl group, an amino group or a hydroxyl group by a chemical bond from a natural or synthetic amino acid.

Herein, the term "treatment" includes prevention, control of progression (prevention of deterioration), improvement (reduction) and cure of the mucosal disorder. The "mucosal disorder" means a condition where morphology, properties and functions to be inherent in the mucosa are disordered in some form. For example, the mucosal disorder can include the conditions such as lesions, defects, erosion, inflammation, ulcers and dryness.

GAG into which the hydrophobic group is introduced via the binding chain, which is contained as the active ingredient in the agent for applying to mucosa of the present invention can be any GAG as long as the GAG binds the group having hydrophobicity derived from a hydrophobic compound having a water, insoluble and oil soluble nature. This hydrophobic group is bound to GAG via the binding chain. As described later, it is not necessary that all constitutive units of GAG bind the hydrophobic groups.

1) GAG

GAG in GAG into which the hydrophobic group is introduced via the binding chain contained in the agent for applying to mucosa of the present invention is an acidic polysaccharide having a repeated long chain structure of disaccharide composed of amino sugar and uronic acid (or galactose). Examples of such GAG include hyaluronic acid, chondroitin, chondroitin sulfate, heparin, heparan sulfate, dermatan sulfate and keratan sulfate, and among them, hyaluronic acid is preferable. These GAG may be pharmaceutically acceptable salts thereof. Examples of such salts include sodium salts, potassium salts, magnesium salts and calcium salts, and among them, the sodium salt is preferable. Therefore, it is the most preferable that GAG in the agent for applying to mucosa of the present invention is sodium hyaluronate. An origin of GAG is not particularly limited, and GAG may be derived from an animal or a microorganism or chemically synthesized. For example, when using sodium hyaluronate, those derived from cock's comb can be exemplified. The molecular weight of GAG is not particularly limited, but its weight average molecular weight is preferably 200,000 to 3,000,000, more preferably 500,000 to 2,000,000 and most preferably 600,000 to 1,200,000. When hyaluronic acid or the pharmaceutically acceptable salt thereof is used, its weight average molecular weight is preferably 200,000 to 3,000,000, more preferably 500,000 to 2,000,000 and most preferably 600,000 to 1,200,000.

2) Hydrophobic Group

The hydrophobic group in GAG into which the hydrophobic group is introduced via the binding chain contained in the agent for applying to mucosa of the present invention is any group as long as the hydrophobic group is derived from the compound havin4, the.water insoluble and oil soluble nature. Examples of such a group can include alkyl groups having 2 to 18 carbon atoms, alkenyl groups having 2 to 18 carbon atoms, alkynyl groups 15 having 2 to 18 carbon atoms, aryl groups, heteroaryl groups, arylalkyl groups, arylalkenyl groups, arylalkynyl groups and amino acid groups.

The alkyl groups having 2 to 18 carbon atoms can include methyl, ethyl, n-propyl, i-propyl, n-butyl, sec-butyl, t-butyl, n-pentyl, t-pentyl, isopentyl, neopentyl, n-heptyl, 5-methylhexyl, 4,4-dimethyl-pentyl, 1,1-dimethyl-pentyl and n-octyl. Among them, the alkyl groups such as n-butyl having 2 to 6 carbon atoms such as n-butyl can be preferably included.

The alkenyl groups having 2 to 18 carbon atoms can include vinyl, 1-propenyl, 2-propenyl, 1-butenyl, 2-methyl-1-propenyl, 1-methyl-1-propenyl, 1-pentenyl, 3-methyl-2-butenyl, 1-heptene-1-yl and 2-heptene-1-yl. Among them, the alkenyl groups such as 1-butenyl having 2 to 6 carbon atoms such as 1-butenyl can be preferably included.

The alkynyl groups having 2 to 18 carbon atoms can include ethynyl, 1-propinyl, 2-propinyl, 1-butynyl, 2-butynyl, 3-butynyl, 1-heptynyl, 2-heptynyl and 3-heptynyl. Among them, the alkynyl groups such as 1-butynyl having 2 to 6 carbon atoms such as 1-butynyl can be preferably included.

The aryl groups can include groups such as phenyl, naphthyl, anthryl and phenanthryl.

The heteroaryl groups can include groups such as furyl, thionyl, thiazolyl, oxazolyl, pyrrolyl, pyridyl, pyrimidinyl and indolyl.

The arylalkyl groups can include groups such as benzyl, phenethyl, naphthylmethyl and naphthylethyl.

The arylalkenyl groups can include groups such as 2-phenyl-ethenyl and p-aminophenylethenyl.

The arylalkynyl groups can include groups such as 2-phenyl-ethynyl and p-aminophenylethynyl.

The amino acid groups can include groups derived from aliphatic amino acids such as glycine, alanine and 3-alanine; branched aliphatic amino acids such as leucine, isoleucine and valine; aromatic amino acids such as phenylalanine and tyrosine; and heterocyclic amino acids such as tryptophan and histidine.

These hydrophobic groups may be monosubstituted or polysubstituted with groups such as hydroxyl, carboxyl, cyano, amino (which may be monosubstituted or disubstituted with the above alkyl), nitro, oxo and alkylcarbonyloxy.

Among the above hydrophobic groups, aryl groups, arylalkyl groups, arylalkenyl groups and arylalkynyl groups which are the hydrophobic groups containing the aryl group can be preferably included, and the arylalkenyl group and the aryl group substituted with the alkylcarbonyloxy group can be particularly preferably included. As such an arylalkenyl group, it is possible to specifically use phenylethenyl and p-aminophenylethenyl. As the aryl group, it is possible to preferably use the groups such as CH3-(CH01-000-phenyl (wherein 1 represents or an integer of 1 to 18).

These hydrophobic groups may also have a function such as ultraviolet ray absorption ability due to having a double bond in the hydrophobic group as shown by a functional group such as phenyl-ethenyl exemplified above contained in the hydrophobic group. For example, when the agent for applying to mucosa of the present invention is used as eye drops described later, it is possible to make the eye drops having the function effectively absorbing the harmful ultraviolet rays by the use of the group having the ultraviolet ray absorption ability as the hydrophobic group. Furthermore, for example, when the agent for applying to mucosa of the present invention is used for the treatment of corneal epithelial layer disorders such as corneal xerosis (dry eye), keratoconjunctivitis, superficial punctate keratitis (SFK), corneal epithelial erosion, corneal epithelial loss and corneal tumor, it is possible to make the agent for applying to mucosa which has pharmacological effects on the above disorders in combination with the function effectively absorbing the harmful ultraviolet rays by the use of the group having the ultraviolet ray absorption ability as the hydrophobic group. As the group having the ultraviolet ray absorption ability, for example, arylalkenyl group having the conjugation double bond which is exemplified by 2-phenyl-ethenyl and p-aminophenylethenyl described above is preferable. When the agent for applying to mucosa of the present invention is used for the corneal disorder, it is preferable that "GAG into which the hydrophobic group is introduced" which is the active ingredient of the agent for applying to mucosa of the present invention is made into an aqueous solution of 0.1% by weight, which blocks 70 to 100% transmission of the ultraviolet rays at a wavelength of 200 to 300 nm when an ultraviolet ray transmittance is measured by the method described in the Example described later. Such a hydrophobic group having the ultraviolet ray absorption ability can preferably include the arylalkenyl groups such as 2-phenyl-ethenyl and p-aminophenylethenyl.

3) Binding Chain

In GAG into which the hydrophobic group is introduced via the binding chain contained in the agent for applying to mucosa of the present invention, the above GAG is bound to the above hydrophobic group via the binding chain. GAG has the functional group which is a carboxyl, hydroxyl or sulfonate (—$SO_3H$) group as the side chain. Thus, the hydrophobic group can be bound to GAG via the binding chain obtained by forming an ether bond, carboxylate ester bond, sulfate ester bond, carboxylic acid amide bond or sulfonate amide bond together with these functional groups. Such a binding chain can specifically include —CONH—, —COO—, —O—, —$SO_3$—, and —$SO_2$NH—. Among them, the carboxylic acid amide bond of —CONH— and the carboxylate ester bond of —COO— can be preferably used, and the carboxylic acid amide bond of —CONH— can be particularly preferably used.

4) Spacer Chain

In GAG into which the hydrophobic group is introduced via the binding chain contained in the agent for applying to mucosa of the present invention, the hydrophobic group is bound to GAG via the above binding chain, and a spacer chain may further exist between the binding chain and the hydrophobic group. As such a spacer chain, any chain group can be used as long as the spacer group does not completely lose the pharmacological effects which GAG has. Specifically, —$(CH_2)_m$— and —$(CH_2)$—$(OCH_2)_n$— (wherein m and n are integers of 1-to 18, respectively) can be included.

These spacer chains can further have the binding chains such as —CONH—, —COO—, —O—, —$SO_3$— and —$SO_2$NH— which are the same as above at the hydrophobic group side. Such a spacer chain having the binding chain at the hydrophobic group side can specifically include —COO—$(CH_2)_m$—, —COO—$CH_2$—$(OCH_2)_n$-1, —CONH—$(CH_2)_m$— and —CONH—$(CH_2)$—$(OCH_2)_n$—.

5) Ratio Having Hydrophobic Group

In GAG into which the hydrophobic group is introduced via the binding chain contained in the agent for applying to mucosa of the present invention, it is not necessary that all of GAG constitutive units respectively have the hydrophobic groups. A ratio of, the bound hydrophobic group in molar equivalent relative to a disaccharide repeat unit in molar equivalent of GAG (hereinafter, referred to as an "introduction ratio") can be optionally determined depending on the type of the hydrophobic group, the degree of required hydrophobicity, the type of the mucosal disorder administered with the agent for applying to mucosa and the administration site, etc. For example, when using a phenylethenyl group which may be substituted as the hydrophobic group, preferably 5 to 30% and more preferably 10 to 20% of a hydrophobic group in molar equivalent is introduced relative to the disaccharide repeat unit in molar equivalent of GAG (in the case where the crosslinking bond described later is not formed).

6) Crosslink Forming Group

In GAG into which the hydrophobic group is introduced via the binding chain contained in the agent for applying to mucosa of the present invention, the hydrophobic group may form a crosslinking bond between GAG molecules by the functional group contained in the group. As the hydrophobic group capable of forming the crosslinking bond, any group can be used as long as the hydrophobic group produces a photodimerization reaction or a photopolymerization reaction by irradiation of ultraviolet rays and is the same as defined above. The hydrophobic group capable of forming the crosslinking bond includes, for example, phenylethenyl, p-aminophenylethenyl, ethenyl, 2-carboxyethenyl and pentane-1,3-dienyl. It is desirable that these groups are bound to GAG via the binding chain which contains the carbonyl group. Among these hydrophobic groups, phenylethenyl or, p-aminophenylethenyl which is bound to GAG via the binding chain which contains the carbonyl group can be particularly preferably used.

In such GAG into which the hydrophobic group is introduced capable of forming the crosslinking bond, GAG molecules can be crosslinked with one another by being subjected to the photodimerization reaction or the photopolymerization reaction by standard methods. For example, according to the methods described in Japanese Published Unexamined Patent Publication No. 2002-249501, the photodimerization reaction or the photopolymerization reaction can be given.

7) Preferable GAG Constitutive Unit

Representatives of GAG into which the hydrophobic group is introduced via the binding chain contained in the agent for applying to mucosa of the present invention can specifically include the agents for applying to mucosa containing GAG into which Ph-CH=CH—COO—$(CH_2)_m$—NH—; Ph-CH=CH—COO—$CH_2$—$(OCH_2)_n$—NH—; Ph-CH=CH—CONH—$(CH_2)_m$—NHCO—; Ph-CH=CH—CONH—$CH_2$—$(OCH_2)_n$—NHCO—; Ph-CH=CH—C00-$(CH_2)_m$; Ph-CH=CH—COO—$CH_2$—$(OCH_2)_n$—O; Ph-CH=CH—CONH—$(CH_2)_m$—O; Ph-CH=CH—CONH—$CH_2$—$(OCH_2)_n$—O; $CH_3$—$(CH_2)_1$—COO-Ph-CONH—$(CH_2)_m$NH or $CH_3$—$(CH_2)_1$—COO-Ph-CONH—$CH_2$—$(OCH_2)$n-NH (wherein Ph represents phenyl group, m and n represent integers of 1 to 18, respectively, and 1 represents 0 or an integer of 1 to 18) is introduced, as the active ingredient.

The following GAG can be included as the representative.

GAG having the repeat unit of the structural unit represented by the Chemical formula 1, as a basic skeleton:

[Chemical formula 1]

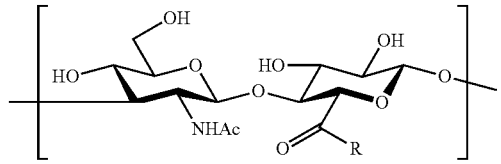

wherein, R represents $R_1$ or $R_2$;
Ac represents an acetyl group;
$R_1$ represents ONa or OH;
$R_2$ represents (1) Ph-CH=CH—COO—$(CH_2)$, —NH—;
(2) Ph-CH=CH—COO—$CH_2$—$(OCH_2)_n$—NH—;
(3) Ph-CH=CH—CONH—$(CH_2)_m$—NH;
(4) Ph-CH=CH—CONH—$CH_2$—$(OCH_2)$, —NH—;
(5) Ph-CH=CH—COO—$(CH_2)$, —O—;

(6) Ph-CH=CH—COO—CH$_2$—(OCH$_2$)$_n$-0-;
(7) Ph-CH=CH—CONH—(CH$_2$)$_m$—O—;
(8) Ph-CH=CH—CONH—CH$_2$—(OCH$_2$)$_n$—O—;
(9) CH$_3$—(CH$_2$)$_l$—COO-Ph-CONH—(CH$_2$)$_m$—NH; or
(10) CH$_3$—(CH$_2$)$_l$—COO-Ph-CONH—CH$_2$—(OCH$_2$)$_n$—NH—;

wherein, Ph represents phenyl group, m and n represent integers of 1 to 18, respectively, and l represents 0 or an integer of 1 to 18, as a basic skeleton, wherein the ratio of the above structural unit wherein R represents R$_2$ is 5 to 30% in molar equivalent relative to the disaccharide repeat unit in molar equivalent of the GAG.

8) Method for Producing GAG into which Hydrophobic Group is Introduced Via Binding Chain To obtain GAG into which the hydrophobic group is introduced via the binding chain, GAG is reacted with a hydrophobic compound in which the above hydrophobic group has been bound to the functional group such as hydroxyl, carboxyl, amino or sulfonate group which can form an ether bond, carboxylate ester bond, sulfate ester bond, carboxylic acid amide bond or sulfonate amide bond together with the carboxyl, hydroxyl or sulfonate (—SO$_3$H) group in GAG. Specifically, when the bond is the carboxylic acid amide bond, GAG having the carboxyl group is reacted with the hydrophobic compound having an amino group to bind the carboxyl group in GAG to the amino group in the hydrophobic compound. In the case of the carboxylate ester bond, GAG is reacted with the hydrophobic compound having hydroxyl or carboxyl group to bind the carboxyl group in GAG to the hydroxyl group in the hydrophobic compound or bind the hydroxyl group in GAG to the carboxyl group in the hydrophobic compound. In the case of the ether bond, GAG having the hydroxyl group is reacted with the hydrophobic compound having the hydroxyl group to react the hydroxyl group in GAG with the hydroxyl group in the hydrophobic compound. In the case of the sulfonate ester bond, GAG is reacted with the hydrophobic compound having the hydroxyl group or sulfonate group to bind the hydroxyl group in GAG to the sulfonate group in the hydrophobic compound or bind the sulfonate group in GAG to the hydroxyl group in the hydrophobic compound. These reactions can be performed by common standard methods, and reaction conditions can be optionally selected by those skilled in the art.

When the spacer chain is present between the binding chain and the hydrophobic group, the order in introducing the spacer chain and the hydrophobic group to GAG is not particularly limited. For example, either the method in which a spacer compound having the functional group such as the hydroxyl, carboxyl, amino or sulfonate group, which can form the ether bond, carboxylate ester bond, sulfate ester bond, carboxylic acid amide bond or sulfonate amide bond together with the functional group in GAG at one end of the above spacer chain is reacted with GAG, and subsequently, the other end of the spacer compound is reacted with the hydrophobic compound which is bound to the functional group such as the hydroxyl, carboxyl, amino, or sultanate group, or the method in which the spacer compound having the functional group such as the hydroxyl, carboxyl, amino or sultanate group which can form an ether bond, carboxylate ester bond; sulfate ester bond, carboxylic acid amide bond or sulfonate amide bond together with the functional group in the hydrophobic compound at one end is reacted with the hydrophobic compound in which the hydrophobic group has been bound to the functional group such as the hydroxyl, carboxyl, amino or sulfonate group, and subsequently the other end of the spacer compound is reacted with GAG may be used. In particular, the method in which the spacer compound is reacted with the hydrophobic compound followed by being reacted with GAG can be preferably used.

The above-described method can be appropriately carried out by publicly known methods, and preferably performed in the presence of a condensing agent. Such a condensing agent can preferably include water soluble carbodiimide such as 1-ethyl-3-(3-dimethylaminopropyl)carbodiimide hydrochloride (EDCI.HC1), condensing agents such as dicyclohexylcarbodiimide (DCC) and N-hydroxysuccinate imide (HOSu). For example, when hyaluronic acid is used as GAG and the cinnamate derivative such as Ph-CH=CH—COO—(CH$_2$)$_m$—NH$_2$ or Ph-CH=CH—COO—CH$_2$—(OCH$_2$)$_n$—NH$_2$ (wherein m and n are integers of 1 to 18,respectively) is used as the hydrophobic compound which is bound to the spacer compound, the condensation method using water soluble carbodiimide such as 1-ethyl-3-(3-dimethylaminopropyl)carbodiimide hydrochloride (EDCI.HCl) and N-hydroxysuccinate imide can be preferably used. The reaction can be accomplished using a mixed solvent of water and a water soluble organic solvent such as dioxane, dimethylformamide or ethanol. The hyaluronate derivative which is highly soluble in an aqueous vehicle can be obtained by treating with a base such as Sodium hydrogen carbonate after the completion of the reaction.

When the thus produced GAG into which the hydrophobic group is introduced via the binding chain is subjected to the photodimerization reaction or the photopolymerization reaction to cross link the GAG molecules with one another, for example, the method described in Japanese Published Unexamined Patent Publication No. 2002-249501 can be used. Specifically, in the case of the compound in which the phenylethenyl group as the hydrophobic group is bound to GAG via —COO—(CH$_2$)$_m$—NHCO—, the crosslink can be formed by irradiating light, to the solution containing them using an ultraviolet lamp.

9) Agent for Applying to Mucosa of the Present Invention

The agent for applying to mucosa of the present invention contains one or more GAG into which the hydrophobic group is introduced via the binding chain as the active ingredient, and may also further include other medically, pharmaceutically or biologically acceptable substances other than the GAG into which the hydrophobic group is introduced via the binding chain. Such substances include but are not limited to, salts such as sodium chloride, potassium chloride, disodium hydrogen phosphate, sodium dihydrogen phosphate and monopotassium hydrogen phosphate, and preservatives such as paraoxybenzoate esters, benzalkonium chloride; chlorobutanol and chlorhexidine glucoriate, and other pharmacologically active ingredients.

The agent for applying to mucosa of the present invention can be made into any publicly known formulation. forms (e.g., solid preparations such as granules and powder, liquid preparations such as aqueous solutions, suspension and emulsion, and gel preparations) as the pharmaceutical for applying to the mucosa. In the agent for applying to mucosa of the present invention, the form thereof upon formulating and distributing and the form thereof upon applying to the mucosa may be the same or different. For example, the agent for applying to mucosa of the present invention may be formulated in the form of solution and may be applied directly to the mucosa as it is. Also, the agent for applying to mucosa of the present invention may be formulated and distributed in the solid form, and may be made into solution or gel when being applied to the mucosa. Thus, the agent for applying to mucosa of the present invention can be made into the formulation form for being prepared when used.

When being made into the liquid agent by dissolving in water, the amount of GAG into which the hydrophobic group is introduced via the binding chain is preferably 0.02 to 5% by weight, more preferably 0.1 to 3% by weight, extremely preferably 0.1 to 1% by weight and most preferably 0.1 to 0.6% by weight.

<Applied Subjects>

The agent for applying to mucosa of the present invention aims at applying to the mucosa. Animals to which the agent for applying to mucosa of the present invention is applied are not particularly limited as long as they have the mucosa, and mammalian animals are preferable. The mammalian animals include, but are not limited to, humans, horses, cattle, dogs, cats, rabbits, hamsters, guinea pigs and mice. The agent for applying to mucosa of the present invention may be of course made into the pharmaceuticals for humans, and can also be made into the pharmaceuticals for the animals. Among them, it is preferable to be made into the pharmaceuticals for humans.

The mucosa to which the agent for applying to mucosa of the present invention can be applied is not particularly limited as long as the mucosa is the mucosa present in the animal. Such mucosa include mucosal tissues present in organs and tissues exemplified by the gastrointestinal system such as the stomach and intestines, the cardiovascular system, the respiratory system, the excretion system such as the urinary bladder, rectum and anus, the genital system such as the vagina, and organs such as eyes, nose and oral cavity which contact with the external world. Among them, the agent for applying to mucosa of the, present invention can be preferably applied to the cornea, conjunctiva, oral cavity mucosa and urinary bladder mucosa.

<Applied Diseases>

The agent for applying to Mucosa of the present invention can be widely applied to such mucosa. The purpose of the application is not particularly limited, and for example, the purposes such as protection of the mucosal tissue (e.g., prevention of snow blindness by ultraviolet rays, pterygium and cataract), prevention of mucosal dryness and the treatment of mucosal disorder Can be exemplified. Thus, the agent for applying to mucosa of the present invention can be applied to not only the mucosa in the abnormal state (e.g., mucosa where the disorder has occurred) but also the mucosa in the normal state. However, since the agent for applying to mucosa of the present invention exerts excellent pharmacological effects in the mucosa where the disorder has occurred, it is possible to preferably use for the treatment of the mucosal disorders, e.g., disorders in the cornea, conjunctiva, oral cavity mucosa and urinary bladder mucosa.

Since the agent for applying to mucosa, of the present invention exerts excellent pharmacological effects particularly on disorders in the mucosal epithelia among the mucosal disorders, it is possible to be preferably used for the treatment of the disorders in the mucosal epithelia.

Examples of such disorders in the mucosal epithelia include corneal epithelial layer disorders such as corneal xerosis (dry eye); keratoconjunctivitis, superficial punctate keratitis (SPK), corneal epithelial erosion corneal epithelial loss and corneal tumor; oral cavity' mucosal disorders such as xerostomia (dry mouth), aphthous ulcer, stomatitis and glossitis; dryness and, pruritus of nasal mucosa; urinary bladder mucosal disorders such as interstitial cystitis; ulcerative proctitis, and dryness of the rectum or vagina. Also dryness and lesions of organ mucosa upon surgical operation can be exemplified. Among them, it is, possible to be preferably used for the treatment of the corneal epithelial layer disorders, the oral cavity mucosal epithelial disorders and the urinary bladder mucosa epithelial layer disorders.

Application Method and Amount

The agent for applying to mucosa of the present invention can be applied to the mucosal tissues exemplified above, and its application method and application formulation can be appropriately determined by those skilled in the art depending on the position, morphology, property and function of the mucosa to be applied, and the purpose of the application. However, it is preferable that the agent for applying to mucosa of the present invention is applied to the mucosa in the liquid form such as solution in use. In that case, upon producing (formulating) or applying the agent for applying to mucosa of the present invention, the liquid can be obtained by dissolving GAG into which the hydrophobic group is introduced via the binding chain in the solvent. The solvent is not particularly limited as long as the solvent can dissolve the GAG into which the hydrophobic group is introduced via the binding chain and is the pharmaceutically acceptable solvent. For example, a buffer such as a phosphate buffer or saline can be used, but the solvent is not limited thereto. In this case, the concentration of the GAG into which the hydrophobic group is introduced via the binding chain in the liquid agent is not particularly limited, and can be appropriately determined depending on the type of the mucosa to be applied and the degree of the mucosal disorder. When the agent for applying to mucosa of the present invention is the eye drops, when the agent for applying to mucosa of the present invention is applied to the oral cavity mucosa or the urinary bladder mucosa, for example, the concentration is preferably 0.02 to 5% by weight, more preferably 0.1 to 3% by weight, still more preferably 0.1 to 1% by, weight, still more preferably 0.1 to 0.6% by weight, extremely preferably 0.1 to 0.5% by weight and most preferably 0.1 to 0.3% by weight.

When the agent for applying to mucosa of the present invention is applied to the mucosa in the stomach as the liquid as above, an oral administration or the administration using a catheter can be selected. When applied to the mucosa in the eye, the nose or the oral cavity, for example, the administration method such as instillation of drop, nasal instillation or oral inclusion can be selected. For example, when the agent for applying to mucosa of the present invention is applied to the mucosa mucosa in the urinary bladder, rectum or vagina, or the mucosa of organs where the dryness is concerned upon surgical operation, the method of administering by injecting, spraying or applying the agent for applying to mucosa of the present invention to a lumen or a surface of these organs or tissues can be selected, but the methods are not limited thereto.

The amount, the number of times and the frequency of the application, (administration of) of the agent for applying to mucosa of the present invention is not particularly limited, and should be determined depending on the mucosa subjected, to the application, the purpose of the application, the, type, age, body weight, gender, and degree of mucosal disorder in the animal to be applied.

Specifically, when the agent for applying to mucosa of the present invention is used for the purpose of treating the human corneal epithelial layer disorder, the agent for applying to mucosa of the present invention at the above-described concentration as the liquid formulation for the instillation of drops (eye drops) containing GAG into which the hydrophobic group is introduced via the binding chain can be administered by instilling 1 to 3 drops per administration 1 to 5 times per day, and may be administered by instilling 1 to 3 drops per administration 1 to 3 times per day.

When the agent for applying to mucosa of the present invention is used for the purpose of treating the human oral cavity mucosal disorder, the agent for applying to mucosa of the present invention at the above-described concentration as the liquid containing GAG into which the hydrophobic group is introduced via the binding chain can be administered by putting the agent for applying to mucosa of the present invention in the oral cavity 1 to 5 times per day and rinsing for approximately several tens of seconds (preferably approximately 20 to 30 seconds) followed by spitting it out.

When the agent for applying to mucosa of the present invention is applied to the urinary bladder mucosal disorder, this is preferably used for the treatment of the urinary bladder mucosal disorders exemplified by non-bacterial refractory cystitis exemplified by interstitial cystitis, eosinophilic cystitis and hemorrhagic cystitis which do not respond to antibacterial agents although symptoms similar to those of acute bacterial cystitis are exhibited. In this case, the agent for applying to mucosa of the present invention at the above-described concentration as the liquid containing GAG into which the hydrophobic group is introduced via the binding chain can be administered by administering the agent for applying to mucosa of the present invention directly to the urinary bladder at the amount of 50 mL per administration 1 to 7 times per week or administering with a catheter in the urinary bladder.

The agent for applying to mucosa of the present invention can stay at the diseased site for a longer period of time because the active ingredient contained in the agent exhibits the high staying property in the mucosa, compared with the conventional drugs containing hyaluronic acid as the active ingredient in which no hydrophobic group has been bound. Therefore, the agent for applying to mucosa of the present invention can also exert the treating effect persistently even at the low administration frequency on the disorders such as inflammation and lesions in the mucosa. However, the agent for applying to mucosa of the present invention is not limited by its administration frequency.

The present invention will be described below by Examples.

EXAMPLE 1

(1-1) Preparation of Cinnamate Derivative-Introduced Sodium Hyaluronate

A 172 mg/5 mL aqueous solution of N-hydroxysuccinimide (HOSu: Watanabe Chemical Industries, Ltd.), a 143 mg/5 mL aqueous solution of 1-ethyl-3-(3-dimethylaminopropyl) carbodiimide hydrochloride (EDCI.HC1) (Watanabe Chemical Industries, Ltd.), and a 181 mg/5 mL aqueous solution of 3-aminopropyl cinnatate hydrochloride (Tokyo Chemical Industry Co., Ltd.) were added to a solution of sodium hyaluronate (1.06 g, 2.7 mmol/disaccharide unit, weight-average molecular weight 900,000; derived from cock's comb, Seikagaku Corporation) in water (115 mL)/dioxane (144 mL). The mixture was stirred for 3 hours and a 750 mg/10 mL aqueous solution of sodium hydrogen carbonate (Japanese Pharmacopoeia) was added. After stirring further 2 h 30 min., the reaction was quenched with acetic acid (214 mg) and sodium chloride (1.0 g). Ethanol (300 mL) was added and the resulting precipitation was filtered off and washed twice successively by 80% ethanol, 95% ethanol. The solid was dried in vacuo at 40° C. over night to afford white solid (1.06 g) (hereinafter in Examples, "cinnamate derivative-introduced sodium hyaluronate" is abbreviated as "cinnamate derivative-introduced HA"). The introduction ratio of the cinnamate derivative was 16%. The introduction ratio of the cinnamate derivative was calculated based on the amount of cinnamate by an absorbance measurement method (wavelength: 269 nm) and the amount of hyaluronate by a carbazole sulfate method.

(1-2) Preparation of Cinnamate Derivative-Introduced HA Solution

Saline was added to 86 mg of cinnamate derivative-introduced HA obtained in the above (1-1) to give a total amount of 15.45 ml, then the solution was shaken over night with a shaker until uniformly dissolved. The 0.5% by weight solution of cinnamate derivative-introduced HA (in drying loss 10%) was obtained. Likewise, the 0.3% by weight and 0.1% by weight solutions of cinnamate derivative-introduced HA were obtained.

EXAMPLE 2

(2-1) Preparation of Cinnamate Derivative-Introduced HA

A 75 mg/5 mL aqueous solution of HOSu, a 62 mg/5 mL WFI solution of EDCI.HC1, and a 92 mg/5 mL WFI solution of 6-aminohexyl cinnamate hydrochloride (Tokyo Chemical Industry Co., Ltd.) were added to a solution of sodium hyaluronate (1.0 g, 2.5 mmol/disaccharide unit, weight-average molecular weight 1,500,000; derived from cock's comb, Seikagaku Corporation) in water for injection (hereinafter referred to as WFI) (150 mL)/dioxane (75 mL). The mixture was stirred for 4 hours and sodium chloride (1.0 g) was added. Ethanol (500 mL) was added and the resulting precipitation was filtered off and washed twice successively by 80% ethanol, ethanol. The solid was dried in vacuo at 40° C. to afford white solid (1.1 g). The introduction ratio of the cinnamate derivative was 2.7%.

(2-2). Preparation of Crosslinked Cinnamate Derivative-Introduced HA

The above cinnamate derivative-introduced HA (12.5 g) was dissolved in phosphate buffered saline (concentration of phosphate: 1.5 mM, hereinafter abbreviated as "PBS") to prepare 2.5% solution of cinnamate derivative-introduced HA (500 mL). The 2.5% solution of cinnamate derivative-introduced HA was irradiated by 800 W high pressure mercury lamp and performed by a heat treatment in an autoclave at 121° C. for 7.5 min. to yield crosslinked cinnamate derivative-introduced HA.

Further, 1 g of the above crosslinked cinnamate derivative-introduced HA was dissolved in 11.5 ml of WFI to prepare the 0.2% by weight of crosslinked, cinnamate derivative-introduced HA.

EXAMPLE 3

(3-1) Preparation of Cinnamate Derivative-Introduced HA

A 172 mg/5 mL aqueous solution of HOSu, a 143 mg/5 mL aqueous solution of EDCI.HC1, and a 181 mg/5 mL aqueous solution of 3-aminopropyl cinnamate hydrochloride (Tokyo Chemical Industry Co., Ltd.) were added to a solution of sodium hyaluronate (1.0 g; 2.5 mmol/disaccharide unit, weight-average molecular weight 900,000; derived from cock's comb, Seikagaku Corporation) in water (150 mL)/ dioxane (75 mL). The mixture was stirred for 3 hours and a 750 mg/10 mL aqueous solution of sodium hydrogen carbonate (Japanese Pharmacopoeia) was added. After stirring further 2 h 30 min., the reaction was quenched with acetic acid (214 mg) and sodium chloride (1.0 g). Ethanol (300 mL) was added and the resulting precipitation was filtered off and washed twice successively by 80% ethanol, 95% ethanol. The solid was dried in vacuo at 40° C. to afford white solid (1.0 g) as cinnamate derivative-introduced HA. The introduction ratio of the cinnamate derivative was 10.1%.

(3-2). Preparation of Fluorochrome-Labeled Cinnamate Derivative-Introduced HA

A 3.0 mmol/mL aqueous solution of HOSu, a 1.5 mmol/mL aqueous solution of EDCI.HCl and a 1.5 mmol/mL aqueous solution of 4-aminofluorescein (Tokyo Chemical Industry Co., Ltd.) were added to a solution of cinnamate derivative-introduced HA obtained in the above (3-1) (1.00 g, 2.5 mmol/disaccharide unit) in water (150 mL)/dioxane (75 mL). The mixture was stirred one day and a 500 mg/10 mL aqueous solution of sodium hydrogen carbonate (Japanese Pharmacopoeia) was added. After stirring further 4 h 30 min., the reaction was quenched with acetic acid (2 mL) and sodium chloride (6.0 g). Ethanol (500 mL) was added and the resulting precipitation was filtered off and washed four times by 80% ethanol, twice by ethanol. The solid was dried in vacuo over night to afford fluorochrome-labeled solid (782 mg) The introduction ratio of the fluorescence was 0.60%.

COMPARATIVE EXAMPLE 1

Preparation of fluorochrome-labeled HA

A 3.0 mmol/mL aqueous solution of HOSu, a 1.5 mmol/mL aqueous solution of EDCI.HCl and a 1.5 mmol/mL, aqueous solution of 4-aminofluorescein (Tokyo Chemical Industry Co., Ltd.) were added to a solution of sodium hyaluronate (1.00 g, 2.5 mmol/disaccharide weight-average molecular weight 900,000; derived from cock's comb, Seikagaku Corporation) in water (150 mL)/dioxane (75 mL). The mixture was stirred one day and a 500 mg/10 mL aqueous solution of sodium hydrogen carbonate (Japanese Pharmacopoeia) was added. After stirring further 4 h 30 min., the reaction was quenched with acetic acid (2 mL) and sodium chloride (6.0 g). Ethanol (500 mL) was added and the resulting precipitation was filtered off and washed four times by 80% ethanol, twice by ethanol. The solid was dried in vacuo, over night to afford fluorochrome-labeled solid (830 mg) The introduction ratio of the fluorescence was 0.32%.

EXAMPLE 4

Measurement of Ultraviolet Ray Transmittance of Cinnamate Derivative-Introduced HA Solution The 0.1% by weight aqueous solution of cinnamate derivative-introduced HA obtained in the above (1-1) was prepared, and the ultraviolet ray transmittance was measured by an spectrometer (UV-1600, Shimadzu Corporation).

A spectrum which indicates the transmittance is shown in FIG. 1, and the transmittance (%) at various wavelengths is shown in Table 1. As a result, 100% of the transmittance was shown at the wavelengths of 340 nm or more, but the transmittance at the wavelengths of approximately 320 nm or less was 20% or less which was extremely low, and it was demonstrated that this solution effectively blocks the transmission of the ultraviolet ray.

In FIG. 1, scales are shown with 65 nm intervals on a horizontal axis and with 20% intervals on a vertical axis.

TABLE 1

| $\lambda$ | T(%) |
|---|---|
| 234 | 19.9 |
| 340 | 106.2 |
| 380 | 101.8 |
| 450 | 98.5 |

In the table, $\lambda$ and T represent the wavelength and the transmittance (%), respectively.

EXAMPLE 5

The Effect of the Cinnamate Derivative-Introduced HA on the Healing of, Rabbit Corneal Epithelium.

The effect of the cinnamate derivative-introduced HA prepared in Example 1 on the healing of rabbit corneal epithelium with surgical removal (The surgical Model).

(5-1) Methods

1) Surgical Removal of Corneal Epithelium (The Surgical Model)

The corneal epithelium of the central region was removed by using a trephine (8 mm I.D), a 23G needle and microscissors after anesthesia with an intravenous injection of 5 mg/kg of ketamine and 2 mg/kg of xylazine and topical administration of 0.4% oxbuprocaine hydrochloride.

2) Topical Administration

One hour and 4 hours after the corneal epithelia were peeled, 150 ul of saline as the control substance was administered in the left eye, and 150 ul of 0.5% by weight cinnamate derivative-introduced HA solution prepared in the above Example (1-2) as the subject substance was administered in the right eye. On one day and 2 days after the peeling, a total of 4 times with 3 hour intervals, and at 3 days after the peeling, with 3 hours interval, the same administration as above was performed. In the administration, 1 ml injection syringes were used. Six model rabbits for the corneal epithelial layer disorder described in the above 1) were used as administration subjects.

3) Photographing of Corneal Epithelial Defective Region

The rabbit was given general anesthesia by intravenously injecting 5 mg/kg of ketamine and 2 mg/kg of xylazine, subsequently, the corneal epithelial loss site was stained with 0.2% sodium fluorescein dissolved in PBS, and photographed under ultra-violet light. The photographing was performed just before the administration of the subject substance one hour after the cornea was peeled and 3 hours after the final administration at 3 days after the peeling. When photographed, a focal length was made constant to make a magnification of photographs constant.

4) Measurement of Corneal Epithelial Defective Region

The area of the corneal epithelial defective region stained with sodium fluorescein was measured on the printed photograph using an image analyzer. A value obtained by subtracting the area of the peeled site 3 hours after the final administration at 3 days after the peeling from the area (peeled area) of the peeled site just before the administration of the subject substance one hour after peeling the corneal epithelia was performed was rendered as "healed area."

(5-2) Study Results

Figure 2:
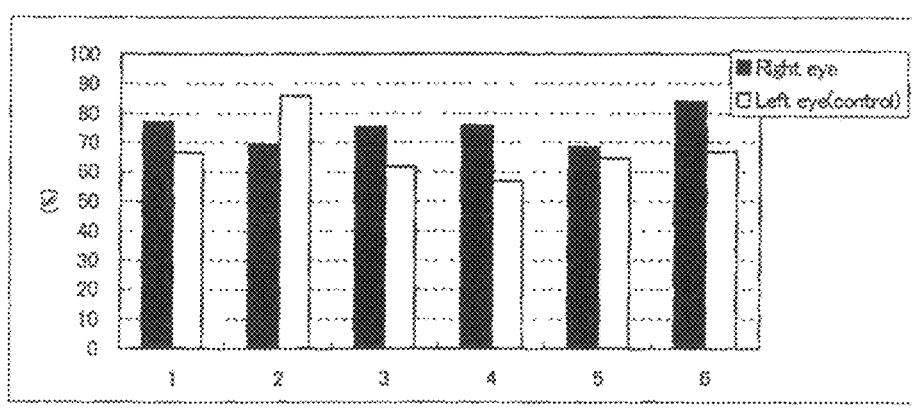
FIG. 2 is a view showing healed area percentages.

The results of a healed area percentage in each individual are shown in FIG. 2, and the results of the healed area percentage and a healed area percentage ratio in each individual are shown in Table 2. The healed area percentage and the healed area percentage ratio were calculated as follows.

Healed area percentage (%)=(Healed area/Peeled area)×100

Healed area percentage ratio=(Healed area percentage in right eye/Healed area percentage in left eye)× 100

TABLE 2

| Specimen Number | Healed area percentage (%) | | Healed area percentage ratio |
|---|---|---|---|
| | right eye (administration of cinnamate derivative-introduced HA) | left eye (administration of saline) | |
| 1 | 76.90 | 66.59 | 115.47 |
| 2 | 69.44 | 85.90 | 80.85 |
| 3 | 75.23 | 61.71 | 121.91 |
| 4 | 75.54 | 56.79 | 133.01 |
| 5 | 68.41 | 64.53 | 106.01 |
| 6 | 83.76 | 66.92 | 125.16 |
| Mean | 74.88 | 67.07 | 113.73 |
| Standard deviation | 5.57 | 9.95 | — |

For each individual of individual numbers 1 to 6, the left column shows the healed area percentage in the right eye (administration of cinnamate derivative-introduced HA), and the right column shows the healed area percentage in the left eye (administration of saline). In FIG. 2 and Table 2, the apparent effect to facilitate the healing of the corneal epithelial layer disorder was observed in 5 of the administered 6 individuals.

EXAMPLE 6

The Effect of the 0.5% Cinnamate Derivative-Introduced HA on the Healing of Rabbit Corneal Epithelium.

The effect of the cinnamate derivative-introduced HA prepared in Example 1 on the healing of rabbit corneal epithelium with surgical removal (The surgical Model).

(6-1) Methods

1) Surgical Removal of Corneal Epithelium (The Surgical Model)

The corneal epithelium of the central region was removed by using a trephine (8 mm I.D), a 23G needle and microscissors after anesthesia with an intravenous injection of 5 mg/kg of ketatine and 2 mg/kg of xylazine and topical administration of 0.4% oxbuprocaine hydrochloride.

2) Topical Administration

One hour and 4 hours after the corneal epithelia were peeled, 150 ul of saline as the control substance was administered in the left eye, and 150 ul of 0.5% by weight cinnamate derivative-introduced HA solution prepared in the above Example (1-2) as the subject substance was administered in the right eye. On one day and 2 days after the peeling a total of 4 times with 3 hour intervals, and at 3 days after the peeling, with 3 hour intervals, the same administration as above was performed. In the administration, the 1 ml injection syringes were used. Fourteen model rabbits for the corneal epithelial layer disorder described in the above 1) were used as the administration subjects.

3) Photographing of Corneal Epithelial Defective Region

The rabbit was given general anesthesia by intravenously injecting 5 mg/kg of ketamine and 2 mg/kg of xylazine, subsequently, the corneal epithelial loss site was stained with 0.2% sodium fluorescein dissolved in PBS, and photographed under ultra-violet light. The photographing was performed just before the administration of the subject substance one hour after the cornea was peeled and 3 hours after the second administration at 1 to 3 days after the peeling. When, photographed, the focal length was made constant to make the magnification of photographs constant.

4) Measurement of Corneal Epithelial Defective Region

The area of the corneal epithelial defective region stained with sodium fluorescein was measured on the printed photograph using the image analyzer. The value obtained by subtracting the area of the peeled site 3 hours after the final administration at 3 days after the peeling from the area (peeled area) of the peeled site just before the administration of the subject substance one hour after the corneal epithelia were peeled was rendered as "healed area."

(6-2) Study Results

Figure 3:
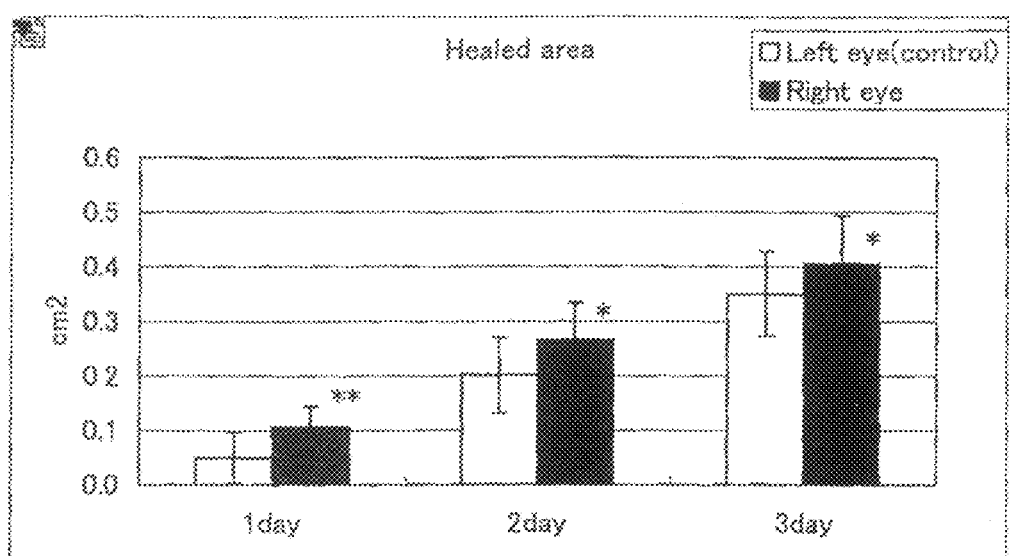
FIG. 3 is a view showing healed areas.
Figure 4:
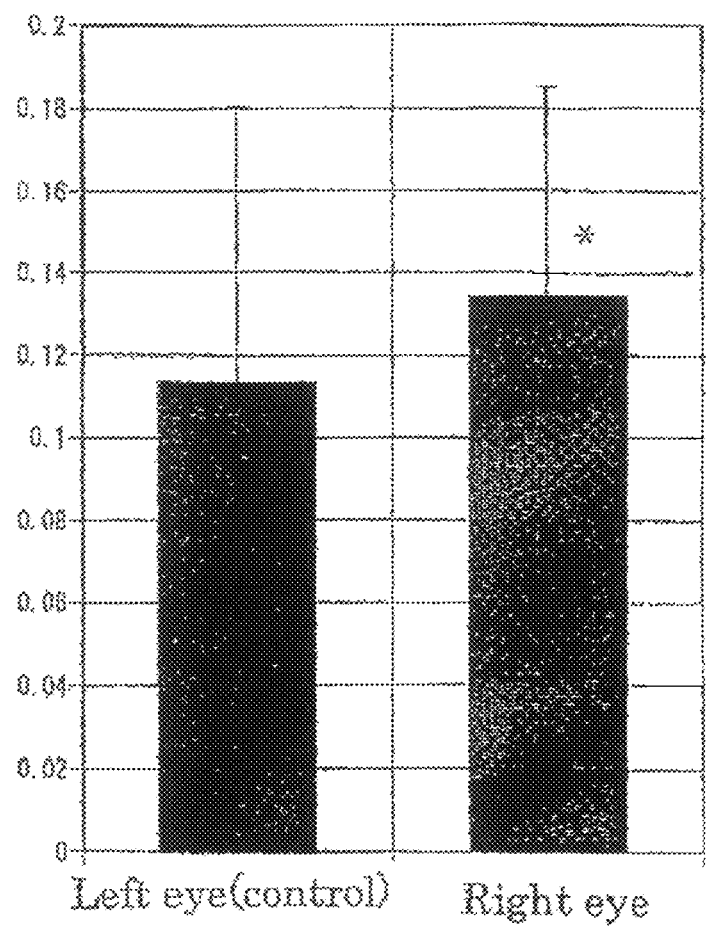
FIG. 4 is a view showing healing rate.

The results of the healed area in each individual are shown in FIG. 3, and the results of a healing rate in each individual are shown in FIG. 4. The healed area and the 20 healing rate were calculated as follows:

Healed area=Area after peeling*−Area at each time point (after 1 to 3 days)

* Herein after, "area after peeling" means 'just before the administration of the subject substance one hour after the cornea was peeled' in calculation of healed area.

Healing rate=Mean of healed areas at respective time points (after 1 to 3 days)

In FIGS. 3 and 4, it was observed that the healed area of the corneal epithelia was significantly increased in the eyes administered with 0.5% by weight cinnamate derivative-introduced HA solution, compared with the healed area of the corneal epithelia in the control eyes. And it was also observed that the healing rate was significantly enhanced in the eyes administered with 0.5% by weight cinnamate derivative-introduced HA solution.

EXAMPLE 7

The Effect of the 0.3% Cinnamate Derivative-Introduced HA on the Healing of Rabbit Corneal Epithelium.

The effect of the cinnamate derivative-introduced HA prepared in Example 1 on the Migration of rabbit corneal epithelium with surgical removal (The surgical Model).

(7-1) Methods

1) Surgical Removal of Corneal Epithelium (The Surgical 10 Model)

The corneal epithelium of the central region was removed by using a trephine (8 mm I.D), a 23G needle and microscissors after anesthesia with an intravenous injection of 5 mg/kg of ketamine and 2 mg/kg of xylaiine and topical administration of 0.4% oxbuprocaine hydrochloride.

2) Topical Administration

One hour and 4 hours after peeling the corneal epithelia, 150 ul of saline as the control substance was administered in the left eye, and 150 41 of 0.3% by weight cinnamate derivative-introduced HA solution prepared in the above Example (1-2) as the subject substance was. administered in the right eye. At one day and 2 days after the peeling, a total of 4 times with 3 hour intervals, and at 3 days after the peeling, with 3 hour intervals, the same administration as above was performed. In the administration, the 1 ml injection syringes were used. Fourteen model rabbits for the corneal epithelial layer disorder described in the above 1) were used as the administration subjects.

3) Photographing of Corneal Epithelial Defective Region

The rabbit was given general anesthesia by intravenously injecting 5 mg/kg of ketamine and 2 mg/kg of xylazine, subsequently, the corneal epithelial loss site was stained with 0.2% sodium fluorescein dissolved in PBS, and photographed under ultra-violet light. The photographing was performed just before the administration of the subject substance one hour after the cornea was peeled and 3 hours after the second administration at 1 to 3 days after the peeling. When photographed, the focal 5 length was made constant to make the magnification of photographs constant.

4) Measurement of Corneal Epithelial Defective Region

The area of the corneal epithelial defective region stained with sodium fluorescein was measured on the printed photograph using the image analyzer. The value obtained by subtracting the area of the peeled site 3 hours after the final administration at 3 days after the peeling from the area (peeled area) of the peeled site just before the administration of the subject substance one hour after the corneal epithelia were peeled was rendered as "healed area."

(7-2) Study Results

Figure 5:
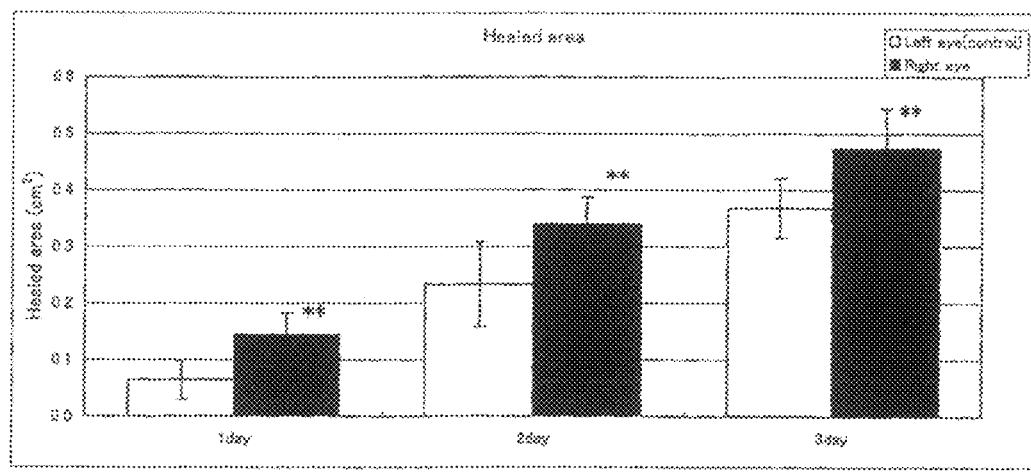
FIG. 5 is a view showing healed areas.
Figure 6:
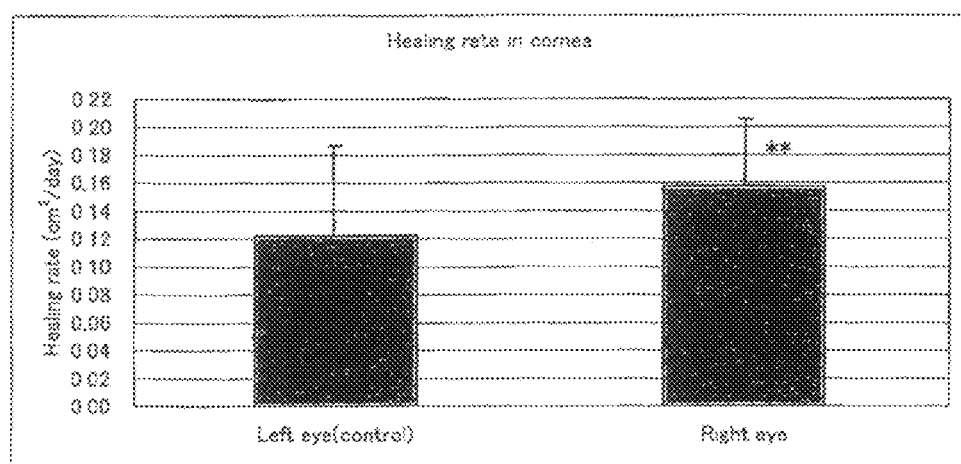
FIG. 6 is a view showing healing rate.

The results of the healed area in each individual are shown in FIG. 5, and the results, of a healing rate in each individual are shown in FIG. 6. The healed area and the healing rate were calculated as follows.

Healed area=Area after peeling−Area at each time point (after 1 to 3 days)

Healing rate=Mean of healed areas at respective time points (after 1 to 3 days)

In FIGS. 5 and 6, it was observed that the healed area of the corneal epithelia was significantly increased in the eyes administered with 0.3% by weight cinnamate derivative-introduced HA solution at all time points of days 1 to 3, compared with the healed area of the corneal epithelia in the control eyes. And it was also observed that the healing rate was significantly enhanced in the eyes administered with 0.3% by weight cinnamate derivative-introduced HA solution.

EXAMPLE 8

The Effect of the 0.1% Cinnamate Derivative-Introduced HA on the Healing of Rabbit Corneal Epithelium (0.1% by Weight Cinnamate Derivative-Introduced HA Aqueous Solution and 0.1% by Weight HA Aqueous Solution, 4 Times of Eye Drops Per Day)

The effect of the cinnamate derivative-introduced HA prepared in Example 1 on the healing of rabbit corneal epithelium with surgical removal (The surgical Model).

(8-1) Methods

1) Surgical Removal of Corneal Epithelium (The Surgical Model)

The corneal epithelium of the central region was removed by using a trephine (8 mm I.D), a 23G needle and microscissors after anesthesia with an intravenous injection of 5 mg/kg of ketamine and 2 mg/kg of xylazine and topical administration of 0.4% oxbuprocaine hydrochloride.

2) Topical Administration

One hour and 4 hours after peeling the corneal. epithelia, 150 ul of an aqueous solution of 0.1% by. weight HA with a weight average molecular weight 600,000 to 1,200,000 as the control substance was administered in the left eye, and 150 ul of 0.1% by weight cinnamate derivative-introduced HA solution prepared in the above Example (1-2) as the subject substance was administered in the right eye. At one day and 2 days after the peeling, a total of 4 times with 3 hour intervals, and at 3 days after the peeling, with 3 hour intervals, the same administration as above was performed. In the administration, the 1 ml injection syringes were used. Eight model rabbits for the corneal epithelial layer disorder described in the above 1) were used as the administration subjects.

3) Photographing of Corneal Epithelial Defective Region

The rabbit was given general anesthesia by intravenously injecting 5 mg/kg of ketamine and 2 mg/kg of xylazine, subsequently, the corneal epithelial loss site was stained with 0.2% sodium fluorescein dissolved in PBS, and photographed under ultra-violet light. The photographing was performed just before the administration of the subject substance one hour after the cornea, was peeled and 3 hours after the second administration at 1 to 3 days after the peeling. When photographed, the focal length was made constant to make the magnification of photographs constant.

4) Measurement of Corneal Epithelial Defective Region

The area of the corneal epithelial defective region stained with sodium fluorescein was measured on the printed photograph using the image analyzer. The value 15 obtained by subtracting the area of the peeled site, 3 hours after the final administration at 3 days after the peeling from the area (peeled area) of the peeled site just before the administration of the subject substance one hour after the corneal epithelia were peeled was rendered as "healed area."

(8-2) Study Results

Figure 7:
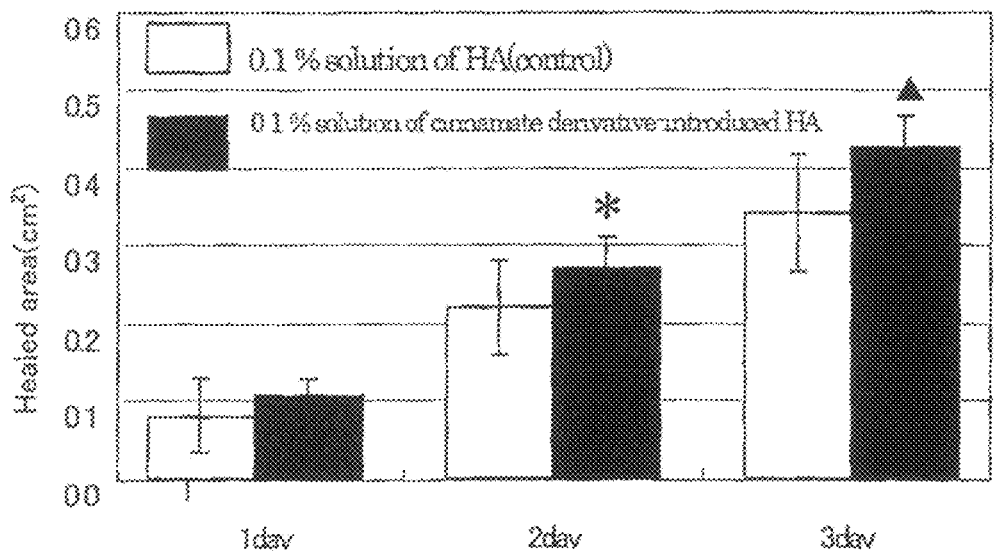
FIG. 7 is a view showing healed areas.
Figure 8:
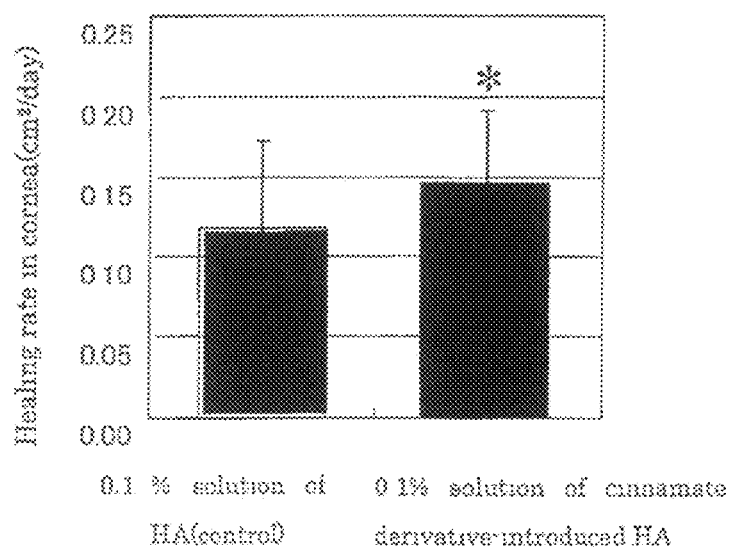
FIG. 8 is a view showing healing rate.

The results of the healed area in each individual are shown in FIG. 7, and the results of the healed area and the healing rate in each individual are shown in FIG. 8. The healed area and the healing rate were calculated as follows.

Healed area=Area after peeling−Area at each time point (after 1 to 3 days)

Healing rate=Mean of healed areas at respective time points (after 1 to 3 days)

In FIGS. 7 and 8, it was observed that the healed area of the corneal epithelia was significantly increased in the eyes administered with 0.1% by weight cinnamate derivative-introduced HA solution, compared with the healed area of the corneal epithelia in the control eyes administered with the 0.1% by weight HA aqueous solution. And it was also observed that the healing rated was significantly enhanced in the eyes administered with 0.1% by weight cinnamate derivative-introduced HA solution.

EXAMPLE 9

The Effect of the 0.1% Cinnamate Derivative-Introduced HA on the Migration of Rabbit Corneal Epithelium (0.1% by Weight Cinnamate Derivative-Introduce a HA Aqueous Solution and 0.1% by Weight HA Aqueous Solution, One Time of Eye Drops Per Day).

The effect of the cinnamate derivative-introduced HA prepared in Example 1 on the Migration of rabbit corneal epithelium with surgical removal (The surgical Model).

(9-1) Methods

1) Surgical Removal of Corneal Epithelium (The Surgical Model)

The corneal epithelium of the central region was removed by using a trephine (8 mm I.D), a 23G needle and microscissors after anesthesia with an intravenous injection of 5 mg/kg of ketamine and 2 mg/kg of xylazine and topical administration of 0.4% oxbuprocaine hydrochloride.

2) Topical Administration

One hour after the corneal epithelia were peeled, 150 ul of the aqueous solution of 0.1% by weight HA with a weight average molecular weight 600,000 to 1,200,000 as the control substance was administered in the left eye, and 150 ul of 0.1% by weight cinnamate derivative-introduced HA solution prepared in the above Example (1-2) as the subject substance was administered in the right eye. Furthermore, at one to 3 days after the peeling, once a day, the same administration as above was performed. In the administration, the 1 ml injection syringes were used. Eight model rabbits for the corneal epithelial layer disorder described in the above 1) were used as the administration subjects.

3) Photographing of Corneal Epithelial Defective Region

The rabbit was given general anesthesia by intravenously injecting 5 mg/kg of ketamine and 2 mg/kg of xylazine, subsequently, the corneal epithelial loss site was stained with 0.2% sodium fluorescein dissolved in PBS, and photographed under ultra-violet light. The photographing was performed just before the administration of the subject substance one hour after the cornea was peeled and 6 hours after the administration at 1 to 3 days after the peeling. When photographed, the focal length was made constant to make the magnification of photographs constant.

4) Measurement of Corneal Epithelial Defective Region

The area of the corneal epithelial defective region stained with sodium fluorescein was measured on the printed photograph using the image analyzer. The value obtained by subtracting the area of the peeled site 3 hours after the final administration at 3 days after the peeling from the area (peeled area) of the peeled site just before the administration of the subject substance one hour after the corneal epithelia were peeled was rendered as the "healed area."

9-2) Results

Figure 9:
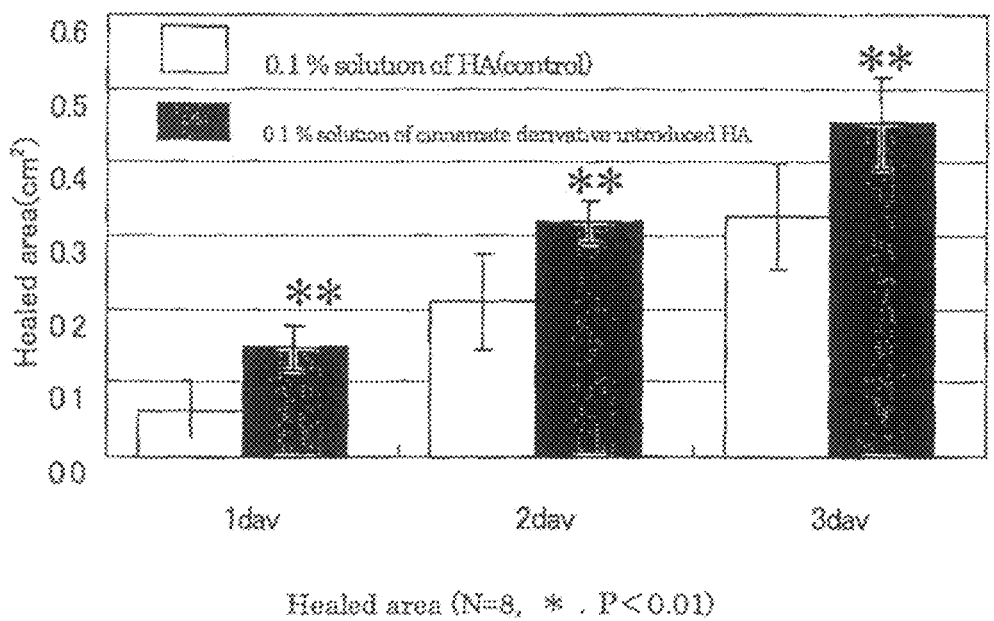
FIG. 9 is a view showing healed areas.
Figure 10:
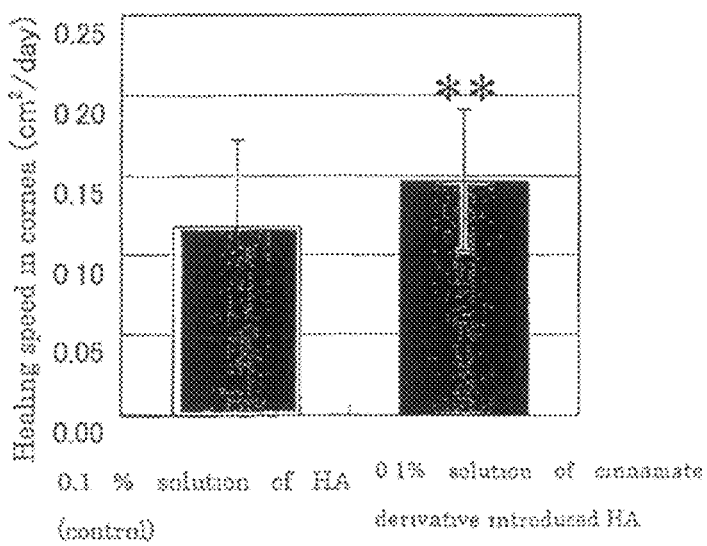
FIG. 10 is a view showing healing rate.

The results of the healed area in each individual are shown in FIG. 9, and the results of the healing rate in each individual are shown in FIG. 10. The healed area and the healing rate were calculated as follows.

Healed area=Area after peeling−Area at each time point (after 1 to 3 days)

Healing rate=Mean of healed areas at respective time points (after 1 to 3 days)

In FIGS. 9 and 10, it was observed that the healed area of the corneal epithelia was significantly increased in the eyes administered with 0.1% by weight cinnamate derivative-introduced HA solution at all time points of the days 1 to 3, compared with the healed area of the corneal epithelia in the control eyes administered with the 0.1% by weight HA aqueous solution. And it was also observed that the healing rate was significantly enhanced in the eyes administered with 0.1% by weight cinnamate derivative introduced HA solution.

EXAMPLE 10

Staying Property at Rabbit Corneal Epithelial Peeling Site Using Fluorescence Labeled Cinnamate Derivative-Introduced HA The effect of the fluorescence labeled cinnamate derivative-introduced HA prepared in Example and the fluorescence labeled HA prepared in Comparative Example 1 on the residual property of rabbit corneal epithelium with surgical removal (The surgical Model).

(101-1) Methods

1) Surgical Removal of Corneal Epithelium (The Surgical Model)

The corneal epithelium of the central region was removed by using a trephine (8 mm I.D), a 23G needle and microscissors after anesthesia with an intravenous injection of 5 mg/kg of ketamine and 2 mg/kg of xylazine and topical administration of 0.4% oxbuprocaine hydrochloride.

2) Topical Administration

One hour after the corneal epithelia were peeled, 150 ul of the aqueous solution of 0.3% by weight fluorescence labeled HA prepared in the above Comparative Example 1 as the control substance was administered in the left eye, and 150 ul of the aqueous solution of 0.3% by weight fluorescence labeled cinnamate derivative-introduced HA prepared in the above Example 3 as the subject substance was administered in the right eye. In the administration, the 1 ml injection syringes were used. Eight model rabbits for the corneal epithelial layer disorder described in the above 1) were used as the administration subjects.

3) Removal of Corneal Epithelia and Production of Frozen Blocks

Two rabbits were given general anesthesia by intravenously injecting 5 mg/kg of ketamine and 2 mg/kg of xylazine per rabbit, and eyeballs were removed 30 minutes, one hour, one and a half hours and 2 hours and 30 minutes after the administration of the subject substance and the control substance. A pore was opened between the cornea and sclera in the removed eyeball using a surgical knife, and only the cornea was taken out using the microscissors. The removed cornea was placed on a biological sample slicing plate (supplied from Nisshin EM Corporation, Cat No. 428), and the portion to be observed was cut out using a single-edged razor blade stainless steel (GEM(R) STAINLESS STEEL UNCOATED, Nisshin EM Corporation, Cat No. 429). The cut out portion was immersed in O.C.T. compound (Tissue-Te) (R)4583, Lot. 1178), then embedded in a cryostat tray (supplied by Murazumi Co., Ltd., Cat. No. 31) filled with the O.C.T. compound so that the portion to be observed was at a bottom, and rapidly frozen using liquid nitrogen in foam polystyrene to make an unfixed frozen block.

4) Production of Frozen Sections

Subsequently, the frozen block was removed from the cryostat tray, and attached on a sample table using the O.C.T. compound. The sample table and a disposable microtome blade (supplied by Leica Microsystems Japan, Model 818, Lot. No. 913212) were set in a high performance frozen microtome for research, and the block was sliced under the condition of a frozen chamber temperature (CT) at −20° C. and sample side temperature (OT) at −16° C. to make sections with a thickness of 5 uM using silane coating slide glasses (supplied by Muto Pure Chemicals Co., Ltd., Star Frost Slide Glass, Cat. No. 5116).

5) Methods of Observation and Photographing

The frozen section was set in an incident-light fluorescence microscope (Olympus Corporation, BH2-RFC), FA images and autofluorescent images were observed at IB cube BH2-DMIB, excitation wavelength: 495 nm, absorption wavelength: 460 nm) and U cube (BH2-DMU, broad band U excitation, absorption wavelength: 435 nm), respectively. The FA image and the autofluorescent image were photographed using a cooled high sensitivity CCD camera (Keyence Corporation, VB-6010) under the condition of exposure time for one second and ISO sensitivity of 200.

(10-2) Study Results

Figure 11:
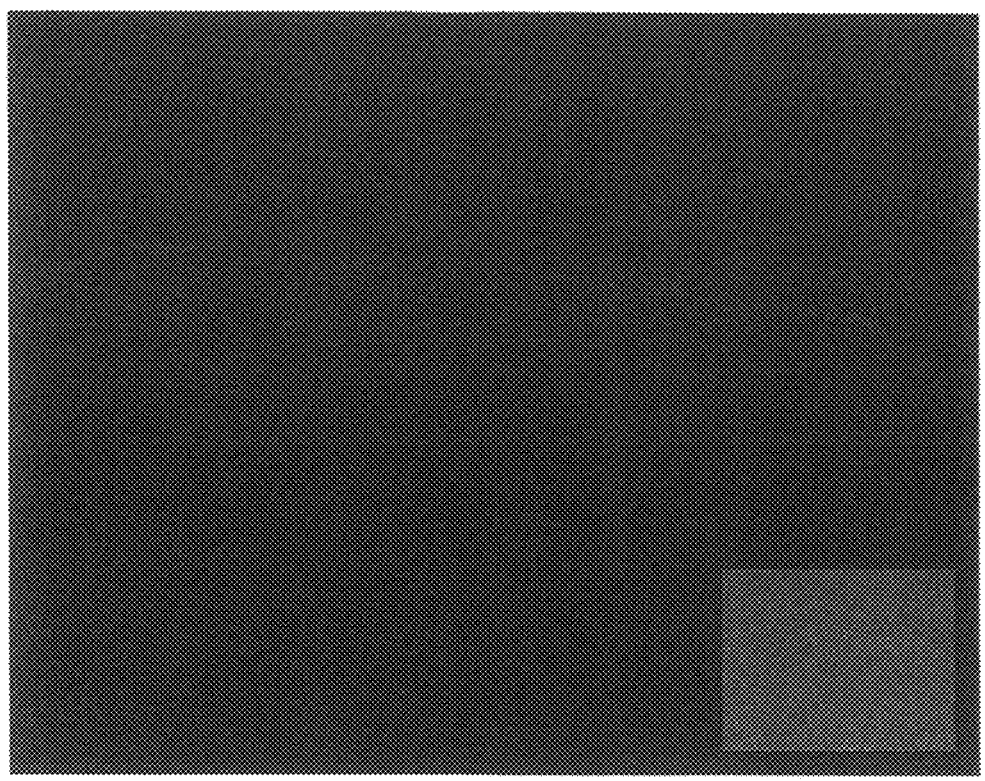
FIG. 11 is a, view showing staying property at peeled sites in rabbit corneal epithelia.
Figure 11:
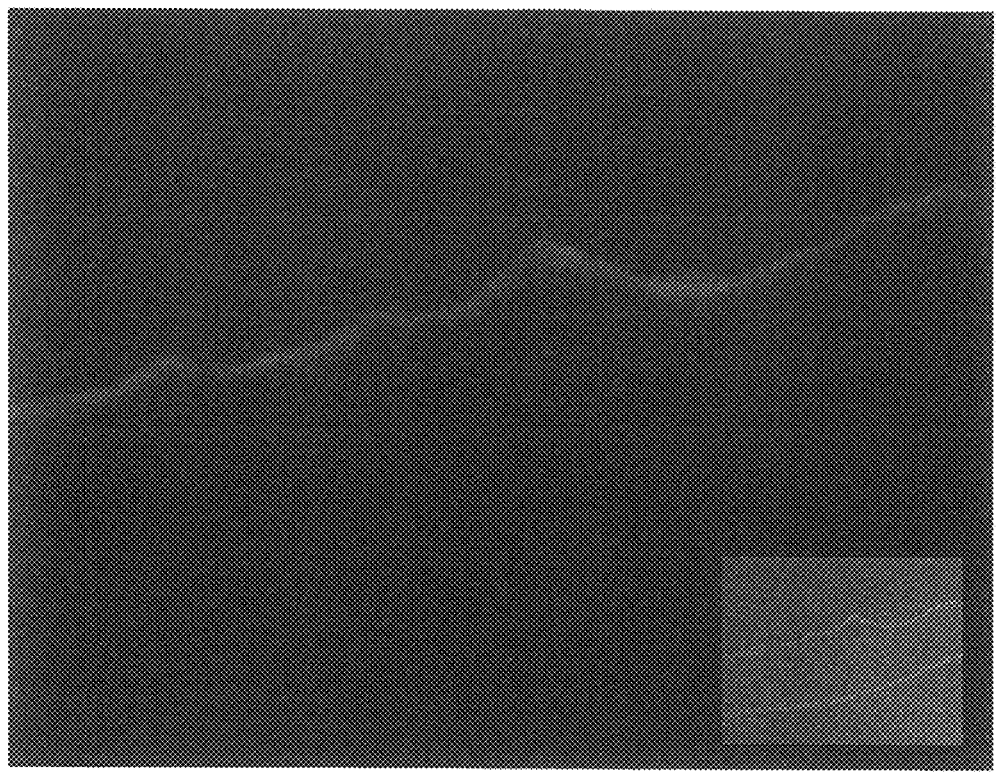
Figure 11:
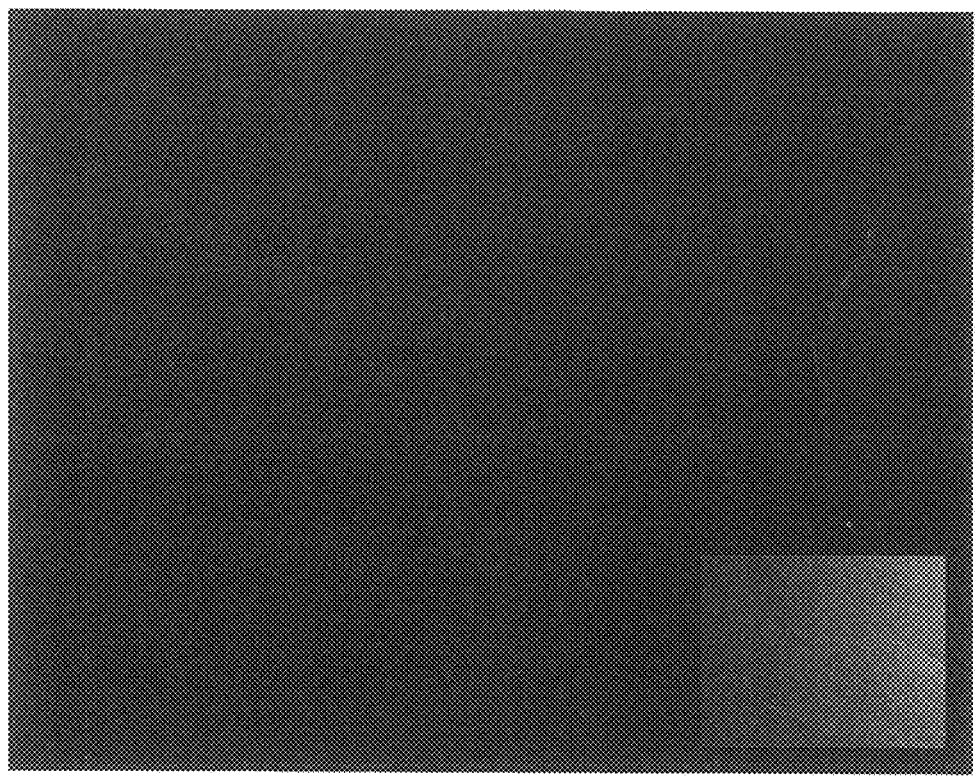
Figure 11:
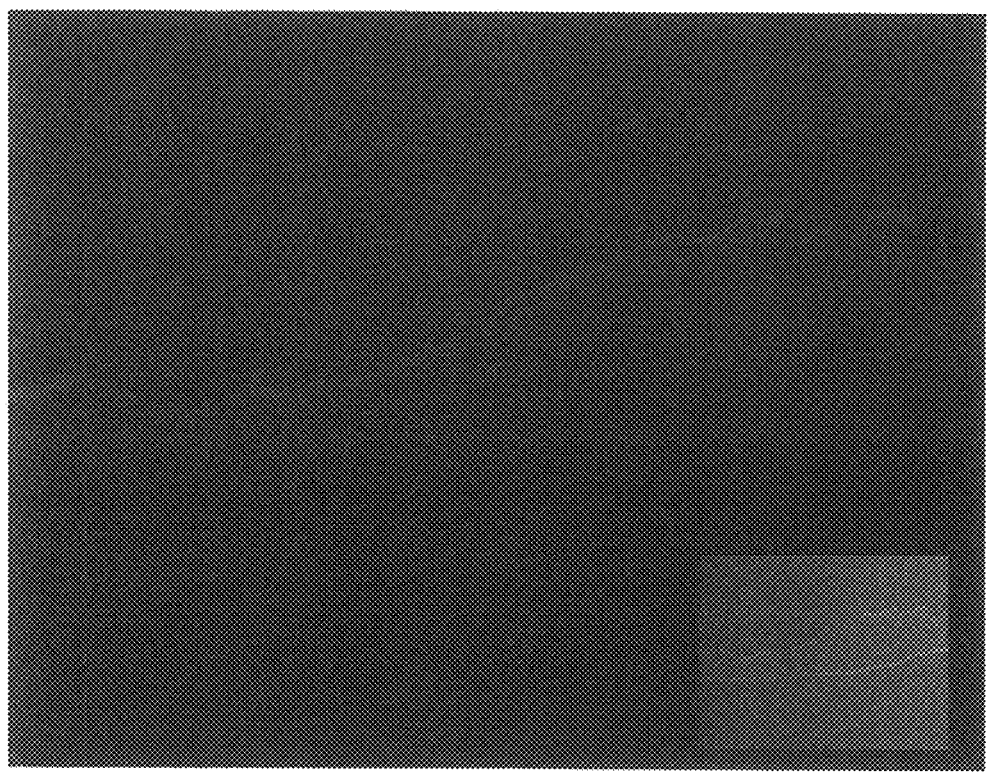
Figure 12:
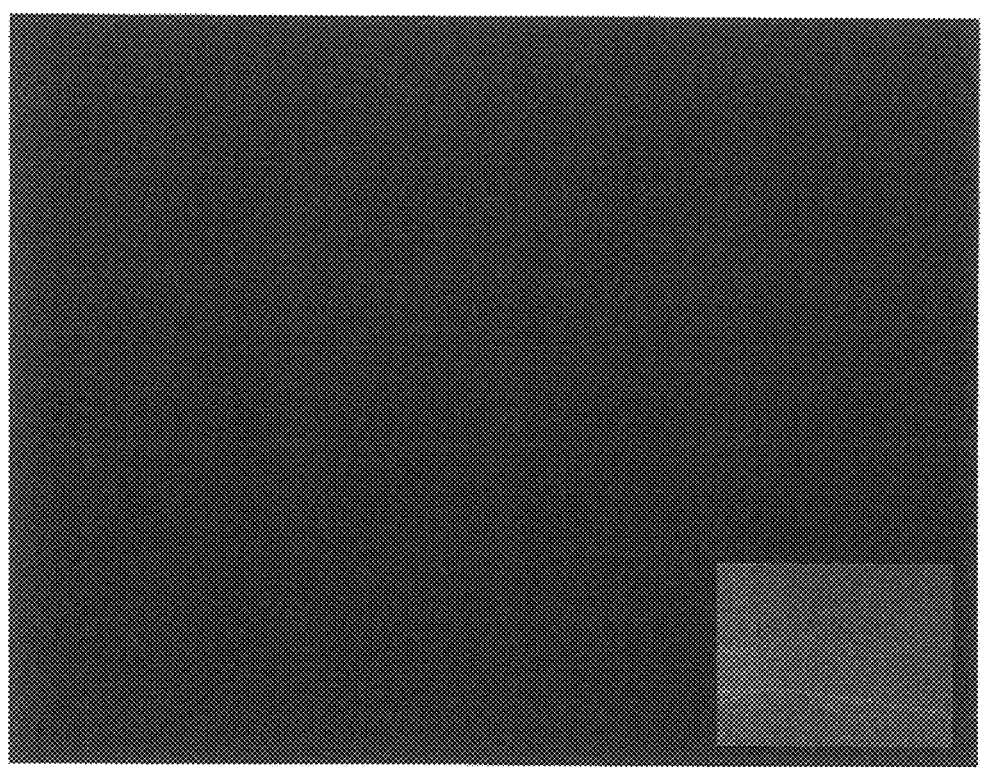
FIG. 12 is a view showing staying property at peeled sites in rabbit corneal epithelia.
Figure 12:
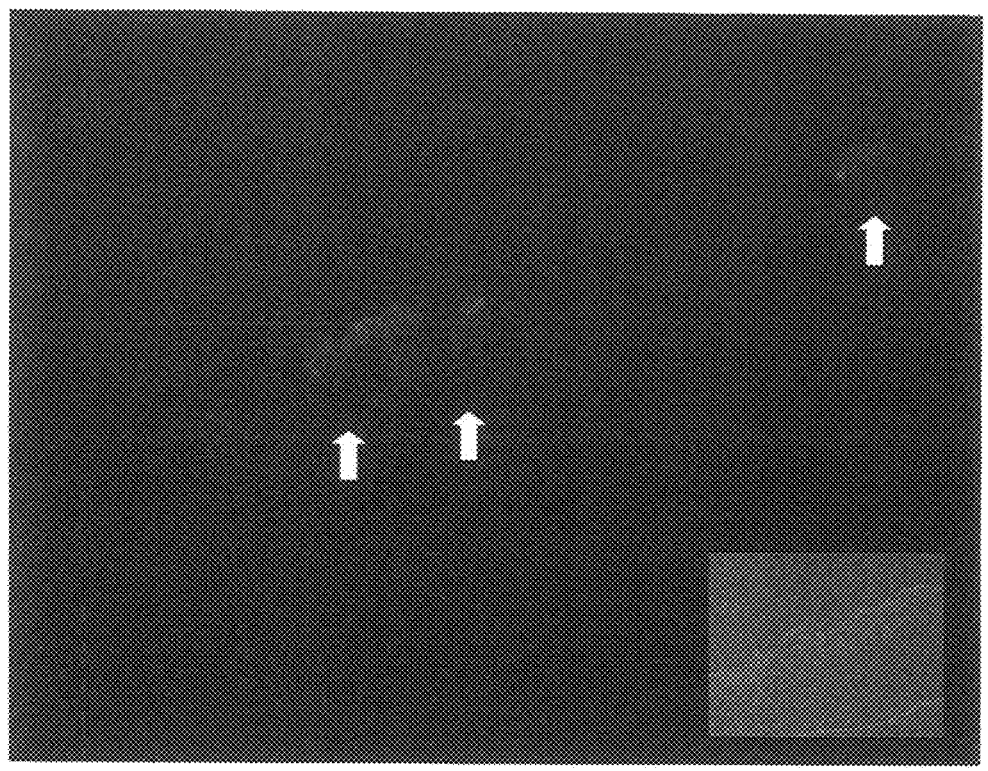
Figure 12:
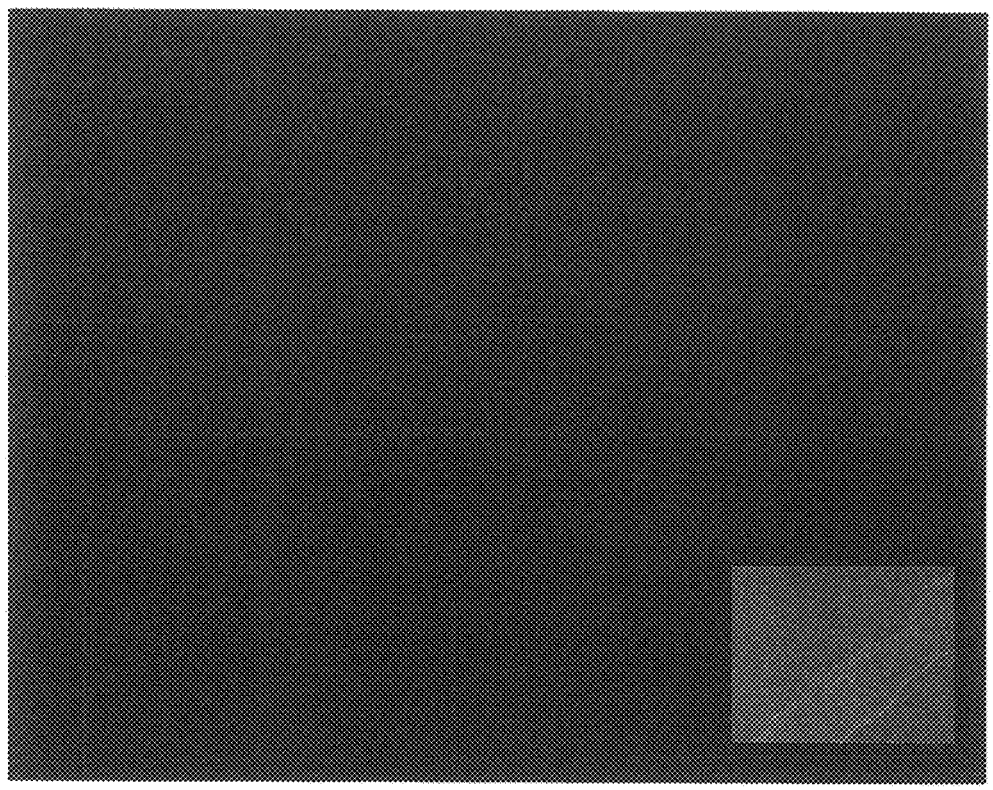
Figure 12:
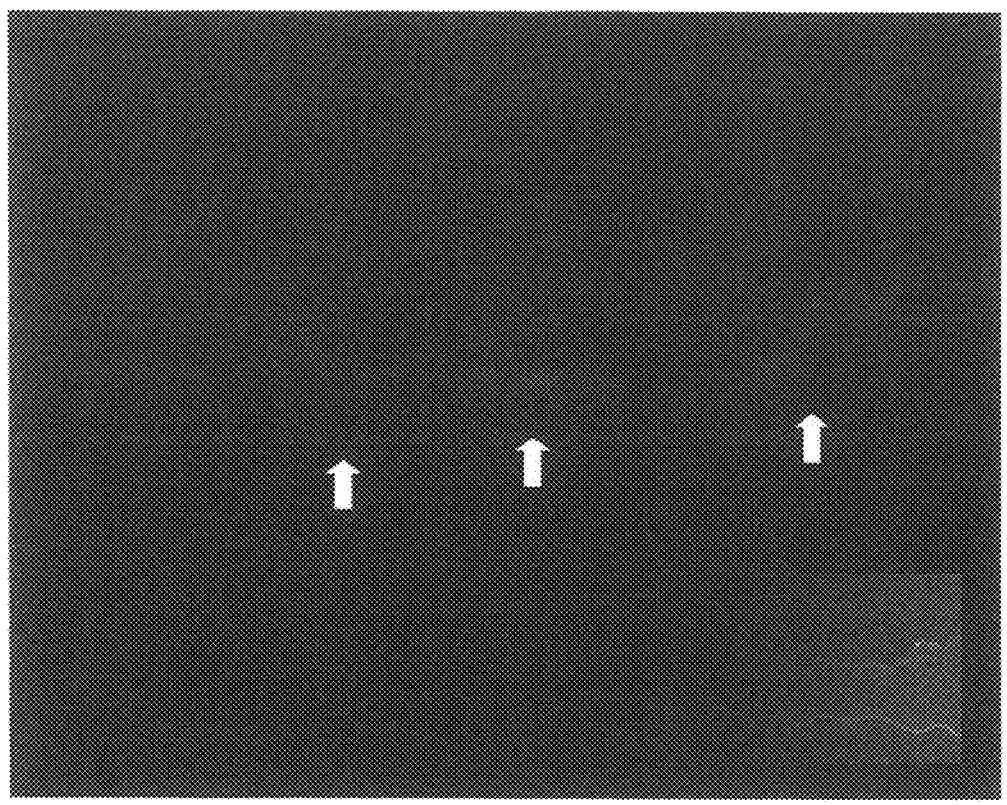

Photographs of the sampled cornea were shown in FIGS. 11 and 12. From FIGS. 11 and 12, it was identified by color development of the fluorescence label that the aqueous solution of 0.3% by weight fluorescence labeled HA which was the control substance stayed until 30 minutes after. the administration but did not stay after one hour. Meanwhile, although the fluorescent color development of the aqueous solution of 0.3% by weight fluorescence labeled cinnamate derivative-introduced HA which was the subject substance was weakened with the elapse of time, the color development was observed at all time points from 30 minutes to 2 hours and 30 minutes after the administration, thereby the high staying performance was confirmed.

EXAMPLE 11

Effect of the 0.3% Cinnamate Derivative-Introduced HA on Rabbit Eyes After Exposure to Ultraviolet Light The protective effect on the cinnamate derivative introduced HA prepared in Example 1 on the rabbit with corneal superficial disorder.

(11-1) Study Procedure

1) Anesthesia and Eyelid Opening in Rabbit

Introduced anesthesia by intravenously injecting 5 mg/kg of ketimine and 2 mg/kg of xylazine and maintained anesthesia by inhalation of isoflurane were given to the rabbit. Subsequently, the eyelid was always opened using an eyelid retractor for kids.

2) Administration of Subject Substance and Control Substance

In the condition where the eye was opened, 150 ul of an aqueous solution of 0.3% by weight HA with a weight average molecular weight 600,000 to 1,200,000 as the control substance was administered in the right eye, and 150 1.11 of 0.3% by weight cinnamate derivative-introduced HA prepared in the above Example (1-2) as the subject substance was administered in the left eye. In the administration, the 1 Ml injection syringes were used. One rabbit described in the above 1) was used as the administration subject.

3) Irradiation of Ultraviolet Rays to Rabbit's Cornea

Ultraviolet rays were irradiated to both eyes from a distance of approximately 10 cm apart from the rabbit eyeball using a 15 kW germicidal lamp. The irradiation was performed for 3 hours.

4) Photographing of Ultraviolet Rays Irradiated Site

The eyeball was stained with 0.2% sodium fluorescein under the continuous anesthesia of the rabbit, and photographed under violet light. When photographed, the focal length was made constant to make the magnification of photographs constant.

(11-2) Study Results

Figure 13:
FIG. 13 is a view showing photographs of an eyeball after irradiation with ultraviolet rays.
Figure 13:
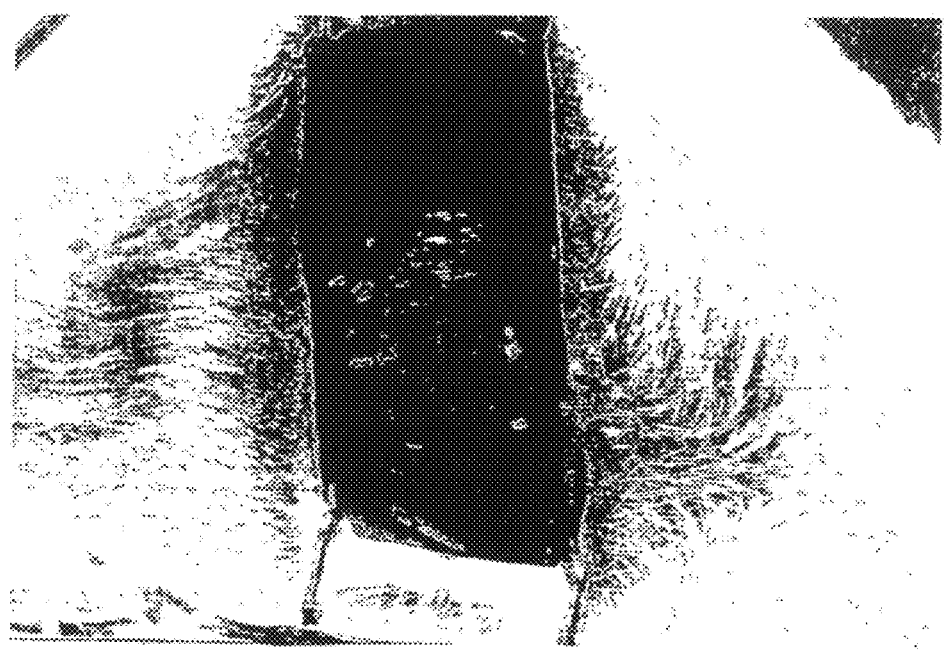

Photographs after the irradiation of the ultraviolet rays were shown in FIG. 13. From FIG. 13, in the eyeball irradiated with the ultraviolet rays after the administration of the control substance, the disordered site stained with 0.2% sodium fluorescein was apparent.

Meanwhile, in the eyeball irradiated with the ultraviolet rays after the administration of the subject substance, the disordered site stained with 0.2% sodium fluorescein clearly smaller than that of the control substance, and the corneal disorder caused by the ultraviolet ray was prevented.

EXAMPLE 12

Moisturizing Effect Using Removed Cornea

Using the removed cornea of the rabbit, the moisturizing performance of the cinnamate derivative-introduced HA prepared in Example 1 was validated.

(12-1) Methods

1) Removal of Cornea

The rabbit was given general anesthesia by intravenously injecting 5 mg/kg of ketamine and 2 mg/kg of xylazine, and the eyeball was removed. A pore was opened between the cornea and the sclera in the removed eyeball using a surgical knife, and only the cornea was taken out using the microscissors.

2) Drying Treatment of Cornea

The drying treatment was performed by placing the removed cornea on a paraffin block with a False-tooth stability material and providing cold air from the distance of approximately 1 m from the cornea using a dryer for 5 minutes.

3) Administration of Test Substances (Subject Substance, Control Substance and Negative Control Substance)

After the completion of the drying treatment, 100 ul of saline as the negative control substance, the aqueous solution of 0.3% by weight HA with a weight average molecular weight of 600,000 to 1,200,000 as the control substance or the aqueous solution of 0.5% by weight cinnamate derivative-introduced HA prepared in the above Example (1-2) as the subject substance was administered to two corneas. In the administration, the 1 ml injection syringes were used. Three rabbits (6 corneas) described in the above 1) were used as the administration subjects.

4) Measurement of Water Evaporation Amount

The water evaporation amount was measured using a water evaporation amount measurement apparatus (AS-TW2, ASAHIBIOMED) before the administration of the test substance, after the drying treatment, after the administration of the test substance and until 40 minutes with 10 minute intervals after the administration of the test substance.

(12-2) Study Results

Figure 14:
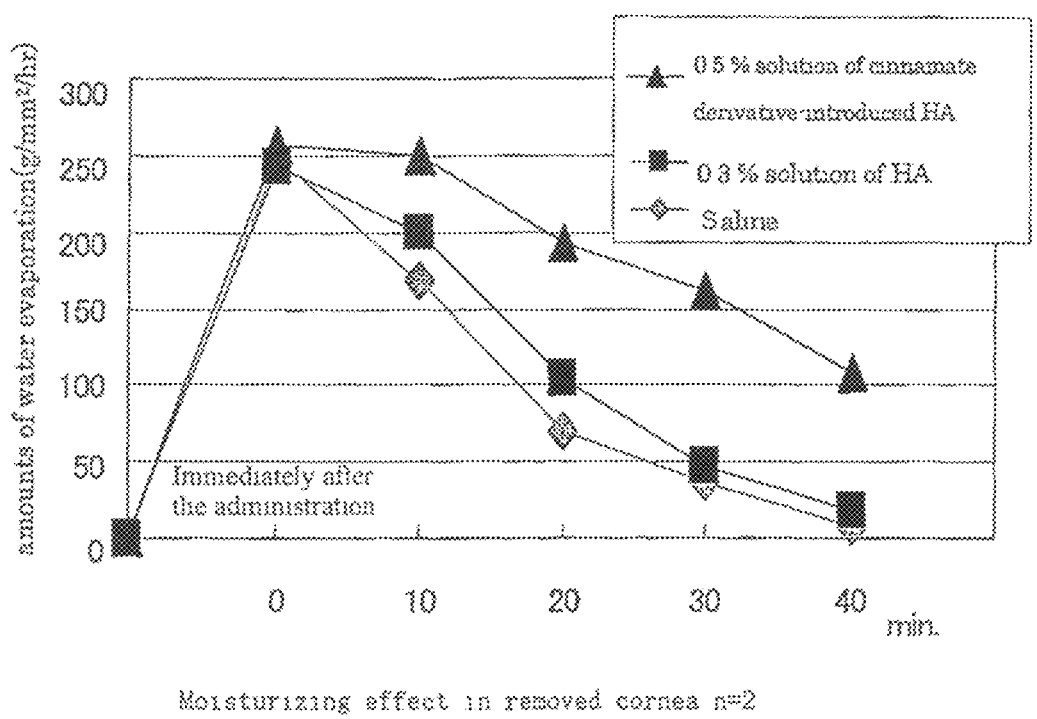
FIG. 14 is a view showing amounts of water evaporation in a removed cornea.

The results of measuring the water evaporation amount were shown in FIG. 14. From FIG. 14, the water evaporation amount was slightly higher in the HA aqueous solution which was the control substance than in the saline which was the negative control whereas the saline became the value close to 0 after 40 minutes. On the other hand, the water evaporation amount after the administration of the subject substance kept the high value even when 40 minutes passed over, thereby the clear moisturizing performance of the subject substance was confirmed.

EXAMPLE 13

(13-1) Methods

1) Removal of Corneal Epithelia

The rabbit was euthanized, and after removing the eyeball, an entire corneal layer was removed by incising along the sclera. The removed cornea was preserved in saline, and the corneal epithelia was fixed by placing it on the paraffin block and the False-tooth stability material just before the measurement (hereinafter described as "the cornea to be measured").

2) Water Evaporation in Corneal Epithelia

The cornea to be measured was given cold air by the dryer from the distance of 30 cm for 5 minutes, and left standing at a room temperature for one hour.

3) Administration of Subject Substance

After the water is evaporated, two drops (approximately 100 ul) of saline as the negative control substance, the aqueous solution of 0.3% by weight HA with a weight average molecular weight of 600,000 to 1,200,000 as the control substance or the aqueous solution of 0.5% by weight cinnamate derivative-introduced HA prepared in the above Example (1-2) as the subject substance was administered by the 1 ml syringe.

4) Measurement of Water Evaporation Amounts

The amount perceived as an unperceived evaporation amount (released water amount per $m_2$ per hour) was directly measured as the water evaporation amount from the cornea to be measured using the water evaporation amount measurement apparatus (AS-TW2).

(13-2) Study Results

Figure 15:
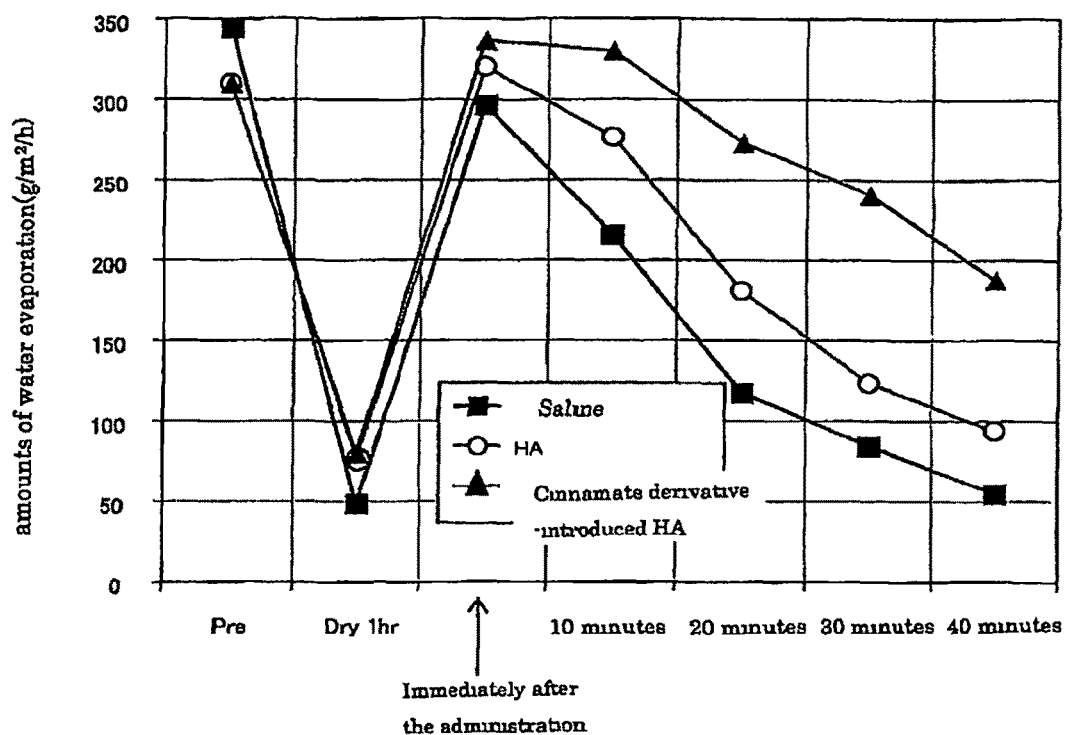
FIG. 15 is a view showing amounts of water evaporation in a removed cornea.

The results of measuring the water evaporation amount were shown in FIG. 15. From FIG. 15, the water evaporation amount was slightly higher in the HA aqueous solution which was the control substance than in the saline which was the negative control whereas the saline exhibited the value close to 0 after 40 minutes. On the other hand, the water evaporation amount of the administered subject substance kept the high value even when 40 minutes had passed over, thereby it was confirmed that the subject substance has a more persistent water retention property on the cornea compared with saline and the HA aqueous solution.

EXAMPLE 14

Validation of Healing Effect of Crosslinked Cinnamate Derivative-Introduced HA

Using a model hamster for xerostomia, the healing effect of the crosslinked cinnamate derivative-introduced HA prepared in Example 2 on the xerostomia was validated.

(14-1) Test Method

1) Production of Model Hamster for Xerostomia

An inside of the oral cavity of a male Syrian hamster was exposed by inserting a test tube with a diameter of approximately 10 mm in the oral cavity close to a buccal side and reversing it under the anesthesia with Nembutal. By giving hot air for approximately 20 seconds, and subsequently giving cold air for 2 minutes and 40 seconds to the exposed, inside of the oral cavity using a dryer, the model hamster for the xerostomia was obtained. The inside of the oral cavity was continuously exposed until the measurement was completed.

2) Administration of Subject Substance and Control Substance

Immediately after making the xerostomia model, 100 ul of (A) PBS, (B) 0.2% by weight HA solution (supplied by Seikagaku Corporation, weight average molecular weight: 1,500,000) or (C) 0.2% by weight crosslinked cinnamate derivative-introduced HA solution was administered by applying to the inside of the oral cavity using a microsyringe.

Hereinafter, the group administered with (A), the 25 group administered with (B) and the group administered with (C) are referred to as PBS group, HA group and crosslinked cinnamate derivative-introduced HA group, respectively. For the administration classification (administration group composition), seven hamsters were used for each of the PBS group, the HA group and the crosslinked cinnamate derivative-introduced HA group.

3) Calculation of Water Evaporation Amount Ratio

The water evaporation amount in the inside of the oral cavity in the xerostomia model hamster was measured using the water evaporation system (Asahibiomed), and the water evaporation amount ratio was calculated when the measurement value immediately after making the xerostomia model hamster was 1. The higher this water evaporation amount ratio is, the more moisturized condition is maintained (degree of oral cavity dryness is low). The measurement was performed immediately after, making the erostomia model hamster, immediately after the administration, 10 minutes and 20 minutes after the administration.

(14-2) Study Results

Figure 16:
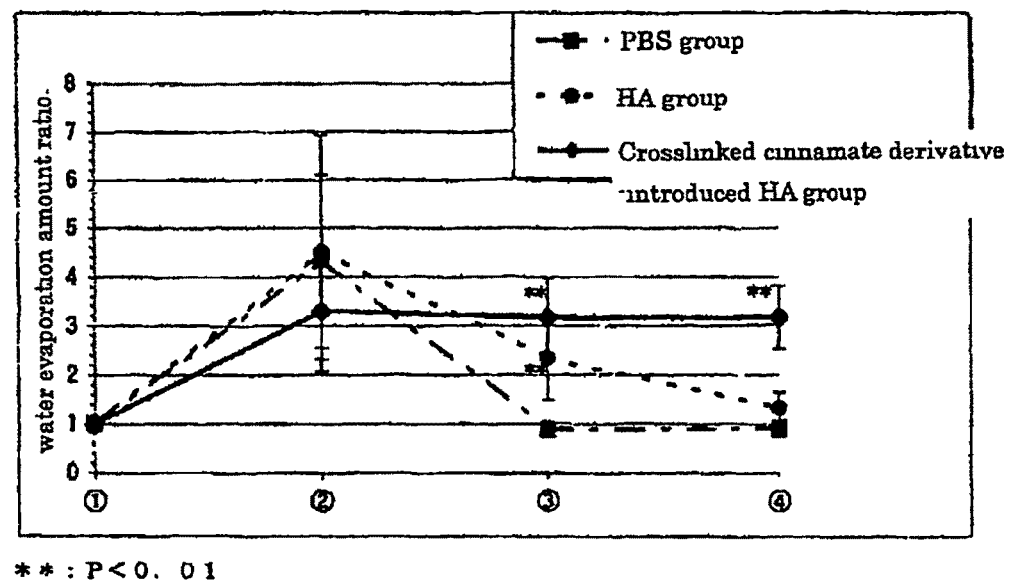
FIG. 16 is a view showing changes in water evaporation amount ratio in model hamsters for xerostomia.

The results of measuring the water evaporation amount are shown in FIG. 16. In the figure, circled numbers 1, 2, 3 and 4 on the horizontal axis represent data immediately after making the xerostomia model hamster, immediately after the administration, 10 minutes and 20 minutes after the administration, respectively. P represents a significance level. Immediately after the administration, all of administration groups exhibited the water evaporation amount ratio of 3.3 to 4.5. The water evaporation amount ratio 10 minutes after the administration was 0.9 on average in the PBS group and 2.3 on average in the HA group. On the other hand, it was 3.2 on average in the crosslinked cinnamate derivative-introduced HA group, thus the higher water evaporation amount ratio than the PBS group and the HA group was shown. Further, the water evaporation amount ratio 20 minutes after the administration was 0.9 on average in the PBS group and 1.3 on average in the HA group. On the other hand, it was 3.2 on average in the crosslinked cinnamate derivative-introduced HA group, thus the extremely higher water evaporation amount ratio compared with the PBS group and the HA group was indicated. Furthermore, as is apparent from FIG. 16, the water evaporation amount ratio in the crosslinked cinnamate derivative-introduced HA group was very stable regardless of the elapse of time. This indicated that the crosslinked cinnamate derivative-introduced HA stayed at-the administered site for a long period of time and exerted a highly persistent effect.

From the above results, GAG into which the hydrophobic group is introduced via the binding chain including the cinnamate derivative-introduced HA and the crosslinked cinnamate derivative-introduced HA has been shown to be suitable for the application to the mucosa and capable of effectively treating the disorder in the mucosal epithelial layer by being applied to the mucosa. It has been also shown that the effect of the treatment is highly persistent.

Since no adverse effect due to the administration of the cinnamate derivative-introduced HA and the crosslinked cinnamate derivative-introduced HA was observed in any of the above animal studies, the safety of the agent for applying to mucosa of the present invention can be sufficiently estimated.

EXAMPLE 15

(15-1) Preparation of Octylamine-Introduced Sodium Hyaluronate

A 25.8 mg/2 mL solution (ethanol:0.1MHC1=I:1) of octylamine, 2 mL of 0.1 M solution (ethanol:water=1:1) of DMT-MM (Wako Pure Chemical Industries, Ltd.) were added to a solution of sodium hyaluronate (502 mg, 1.25 mmol/disaccharide unit, weight-average molecular weight 900,000) in water (50 mL)/ethanol (50 mL). The mixture was stirred over night and a 376 mg/5 mL aqueous solution of sodium hydrogen carbonate (Japanese Pharmacopoeia) was added. After stirring further 5 hours, the reaction was quenched with acetic acid (107 mg) and sodium chloride (522 mg). Ethanol (250 mL) was added and the resulting precipitation was filtered off and washed twice successively by 80% ethanol, ethanol. The solid was dried in vacuo to afford white solid (475 mg). The introduction ratio of octylamine was 12.6% by HPLC.

(15-2) Preparation of Hexadecylamine-Introduced Sodium Hyaluronate

A 30 mg/3 mL solution (ethanol:0.1MHC1=1:1) of octylamine, 1.25 mL of 0.1 M solution (ethanol:water=1:1) of DMT-MM (Wako Pure Chemical Industries, Ltd.) were added to a solution of sodium hyaluronate (501 mg, 1.25 mmol/disaccharide unit, weight-average molecular weight 900,000) in water (50 mL)/ethanol (50 mL). The mixture was stirred over night and a 381. mg/5 mL aqueous solution of sodium hydrogen carbonate (Japanese Pharmacopoeia) was added. After stirring further 5 hours, the reaction was quenched with acetic acid (107 mg) and sodium chloride (497 mg): Ethanol (250 ML) was added and the resulting precipitation was filtered off and washed twice successively by 80% ethanol, ethanol. The solid was dried in vacuo to afford white solid (497 mg). The introduction ratio of hexadecylamine was 12% by HPLC.

(15-3) Preparation of Sample Solution 64 mg of compound obtained in the above (15-1) was added to 5 mM phosphate buffer saline to give a total amount of 59 ml, then the solution was shaken over night with a shaker. The 0.1% by weight solution of compound prepared in the above (15-1) was obtained.

Likewise, 0.1% by weight solution of compound prepared in the above (15-2) was obtained.

EXAMPLE 16

The Effect of the 0.1% Cinnamate Derivative-Introduced HA on the Healing of Rabbit Corneal Epithelium.

The effect of the cinnamate derivative-introduced. HA prepared in Example 1 on the healing of rabbit corneal epithelium with surgical removal (The surgical Model).

(16-1) Methods

1) Surgical Removal of Corneal Epithelium (The Surgical Model)

The corneal epithelium of the central region was removed by using a trephine (8 mm I.D), a 23G needle and microscissors after anesthesia with an intravenous injection of 5 mg/kg of ketamine and 2 mg/kg of xylazine and topical administration of 0.4% oxbuprocaine hydrochloride.

2) Topical Administration

One hour and 4 hours after peeling the corneal epithelia, 150 ul of saline as the control substance was administered in the left eye, and 150 ul of 0.1% by weight cinnamate derivative introduced HA solution prepared in the above Example (1-2) as the subject substance was administered in the right eye. At one day and 2 days after the peeling, a total of 4 times with 3 hour intervals, and at 3 days after the peeling, with 3 hour intervals, the same administration as above was performed. In the administration, the 1 ml injection syringes were used. Fourteen model rabbits for the corneal epithelial layer disorder described in the above 1) were used as the administration subjects.

3) Photographing of Corneal Epithelial Defective Region

The rabbit was given general anesthesia by intravenously injecting 5 mg/kg of ketamine and 2 mg/kg of xylazine, subsequently, the corneal epithelial loss site was stained with 0.2% sodium fluorescein dissolved in PBS, and photographed under ultra-violet light. The photographing was performed just before the administration of the subject substance one hour after the cornea was peeled and 3 hours after the second administration at 1 to 3 days after the peeling. When photographed, the focal length was made constant to make the magnification of photographs constant.

4) Measurement of Corneal Epithelial Defective Region

The area of the corneal epithelial defective region stained with sodium fluorescein was measured on the printed photograph using the image analyzer. The value obtained by subtracting the area of the peeled site 3 hours after the final administration at 3 days after the peeling from the area (peeled area) of the peeled site just before the administration of the subject substance one hour after the corneal epithelia were peeled was rendered as "healed area."

(16-2) Study Results

Figure 17:
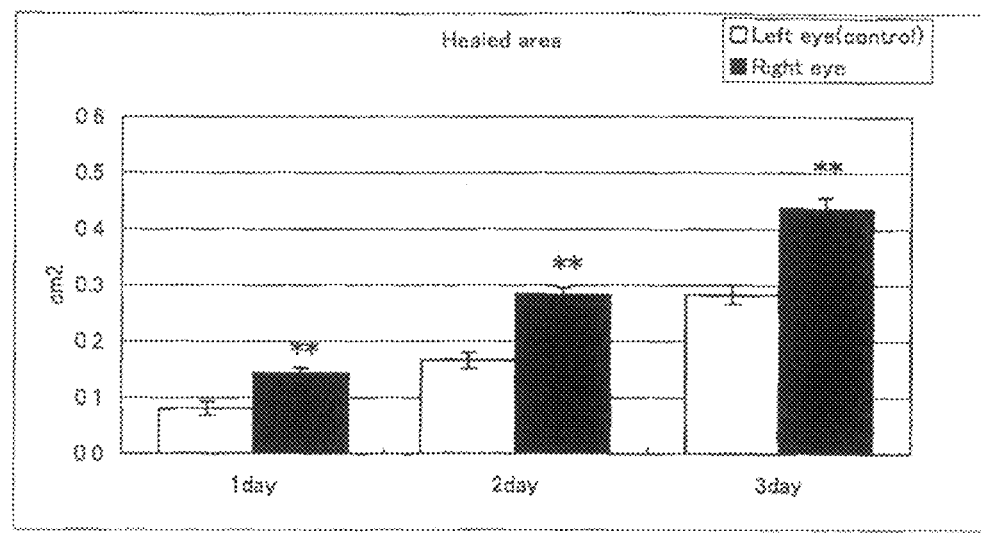
FIG. 17 is a view showing healed areas.
Figure 18:
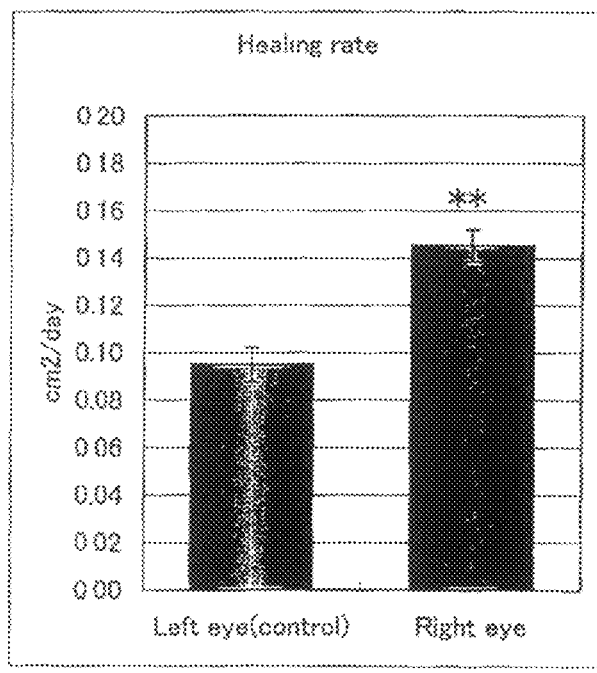
FIG. 18 is a view showing healing rate.

The results of the healed area in each individual are shown in FIG. 17, and the results of a healing rate in each individual are shown in FIG. 18. The healed area and the healing rate were calculated as follows.

Healed area=Area after peeling−Area at each time point (after 1 to 3 days)

Healing rate=Mean of healed areas at respective time points (after 1 to 3 days)

In FIGS. 17 and 18, it was observed that the healed area of the corneal epithelia was significantly increased in the eyes administered with 0.1% by weight cinnamate derivative-introduced HA solution at all time points of days 1 to 3, compared with the healed area of the corneal epithelia in the control eyes. And it was also observed that the healing rate was significantly enhanced in the eyes administered with 0.1% by weight cinnamate derivative-introduced HA solution.

EXAMPLE 17

The Effect of the 0.1% Octylamine-Introduced HA and Hexadecylamine-Introduced HA on the Healing of Rabbit Corneal Epithelium.

The effect of the octylamine-introduced HA and hexadecylamine-introduced HA prepared in Example 15 on the healing of rabbit corneal epithelium with surgical removal (The surgical Model).

(17-1) Methods

1) Surgical Removal of Corneal Epithelium (The Surgical Model)
The corneal epithelium of the central region was removed by using a trephine (8 mm I.D), a 23G needle and microscissors after anesthesia with an intravenous injection of 5 mg/kg of ketamine and 2 mg/kg of xylazine and topical administration of 0.4% oxbuprocaine hydrochloride.
2) Topical Administration
One, hour and 4 hours after peeling the corneal epithelia, 150 ul of saline as the control substance was administered in the left eye; and 150 ul, of 0.1% octylamine-introduced HA and hexadecylamine-introduced HA solution prepared in the above Example (15-2) as the subject substance was administered in the right eye. At one day and 2 days after the peeling, a total of 4 times with 3 hour intervals, and at 3 days after the peeling, with 3 hour intervals, the same administration as above was performed. In the administration, the 1 ml injection syringes were used. Eight model each rabbits for the corneal epithelial layer disorder described in the above 1) were used as the administration subjects.
3) Photographing of Corneal Epithelial Defective Region
The rabbit was given general anesthesia by intravenously injecting 5 mg/kg of ketamine and 2 mg/kg of xylazine, subsequently, the corneal epithelial loss site was stained with 0.2% sodium fluorescein dissolved in PBS, and photographed under ultra-violet light. The photographing was performed just before the administration of the subject substance one hour after the cornea was peeled and 3 hours after the second administration at 1 to 3 days after the peeling. When photographed, the focal length was made constant to make the magnification of photographs constant.
4) Measurement of Corneal Epithelial Defective Region
The area of the corneal epithelial defective region stained with sodium fluorescein was measured on the printed photograph using the image analyzer. The value obtained by Subtracting the area of the peeled site 3 hours after the final administration at 3 days after the peeling from the area (peeled area) of the peeled site just before the administration of the subject substance one hour after the corneal epithelia were peeled was rendered as "healed area."

(17-2.) Study Results

Figure 19:
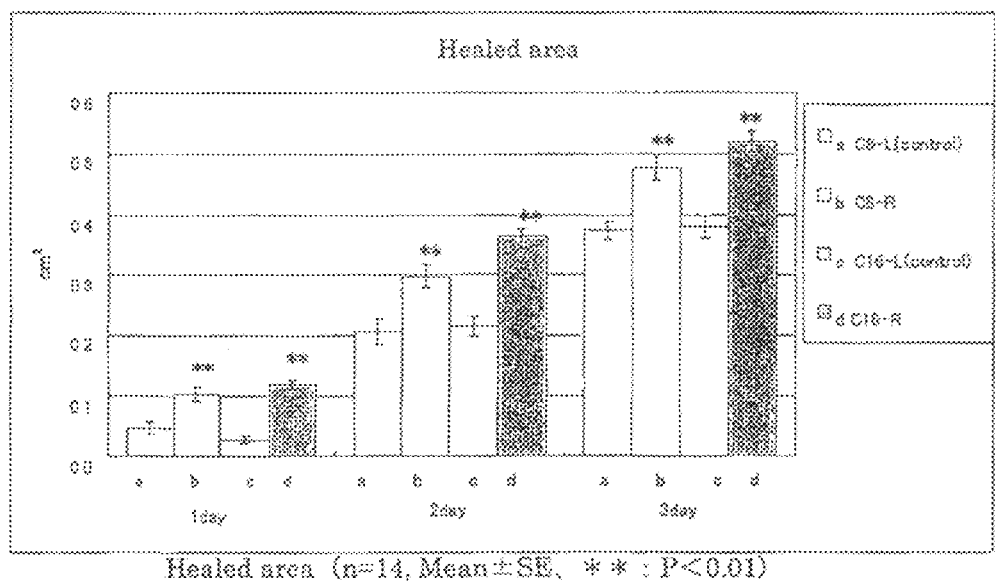
FIG. 19 is a view showing healed areas.
Figure 20:
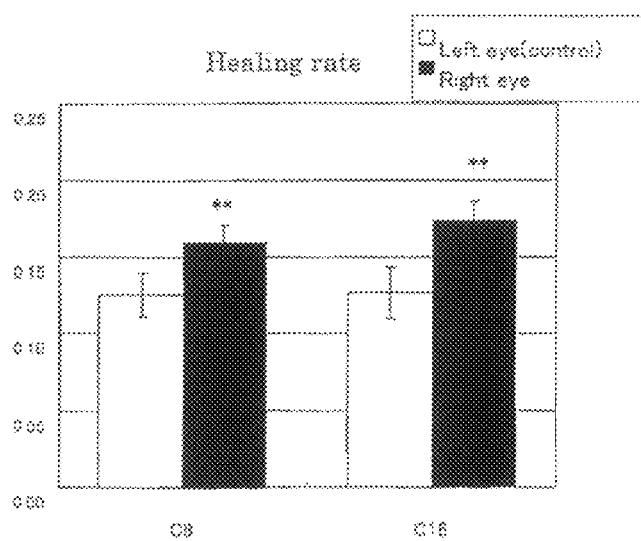
FIG. 20 is a view showing healing rate.

The results of the healed area in each individual are shown in FIG. 19, and the results of a healing rate in each individual are shown in FIG. 20. In FIG. 19, C8-L(a: control), C8-R(b), C16-L(c: control), C16-R(d) represents left eye to which saline was administrated as a control for C8-R, right eye to which 0.1% octylamine-introduced HA solution was administrated, left eye to which saline was administrated as a control for C16-R, right eye to which 0.1% hexadecylamine-introduced HA solution was administrated, respectively. In FIG. 20, C8 represents results of the above study using octylamine, and C16 represents results of the above study using hexadecylamine. The healed area and the healing rate were calculated as follows.

Healed area=Area after peeling−Area at each time point (after 1 to 3 days)

Healing rate=Mean of healed areas at respective time points (after 1 to 3 days)

In FIGS. 19 and 20, it was observed that the healed area of the corneal epithelia was significantly increased in the eyes administered with 0.1% octylamine-introduced HA and hexadecylamine-introduced HA solution at all time points of days 1 to 3, compared with the healed area of the corneal epithelia in the control eyes. And it was also observed that the healing rate was significantly enhanced in the eyes administered with 0.1% octylamine-introduced HA or hexadecylamine-introduced HA solution.

What is claimed is:

1. A method for the reduction of a corneal epithelial layer disorder, comprising administering to a subject in need thereof an effective amount of a glycosaminoglycan into which a hydrophobic group is introduced via a binding chain into a repeating unit of the glycosaminoglycan with a degree of substitution of 10% to 20% in molar equivalent of the glycosaminoglycan, wherein the glycosaminoglycan is hyaluronic acid or a salt thereof, the binding chain is —CONH—, the hydrophobic group is a phenylethenyl group, the glycosaminoglycan into which a hydrophobic group is introduced via a binding chain further includes a spacer chain between the binding chain and the hydrophobic group, wherein the spacer chain is —(CH$_2$)$_3$—OC(=O)—,
wherein said glycosaminoglycan into which a hydrophobic group is introduced contains repeating units of formula (I):

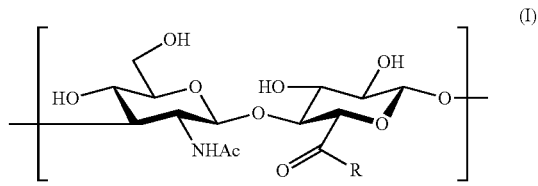

wherein R is —OH, —NH—(CH$_2$)$_3$—OC(=O)—CH=CH—Ph, or a salt of said —OH, and
wherein said corneal epithelial layer disorder is corneal xerosis, keratoconjunctivitis, superficial punctate keratitis, corneal epithelial erosion, or corneal epithelial loss.

2. The method of claim 1 wherein the glycosaminoglycan is sodium hyaluronate.

3. The method of claim 1 or 2, wherein said glycosaminoglycan into which a hydrophobic group is introduced is administered in a composition in which the concentration of said glycosaminoglycan into which a hydrophobic group is introduced is 0.02 to 5% by weight.

4. The method of claim 3, wherein said glycosaminoglycan into which a hydrophobic group is introduced is administered in a composition in which the concentration of said glycosaminoglycan into which a hydrophobic group is introduced is 0.1 to 0.6% by weight.

* * * * *

UNITED STATES PATENT AND TRADEMARK OFFICE
CERTIFICATE OF CORRECTION

PATENT NO.         : 8,969,319 B2
APPLICATION NO.    : 13/070210
DATED              : March 3, 2015
INVENTOR(S)        : Kenji Miyamoto et al.

It is certified that error appears in the above-identified patent and that said Letters Patent is hereby corrected as shown below:

Title Page, item (75) Inventors:
"Katsuya Takahishi"
should read as
--Katsuya Takahashi--

Signed and Sealed this
Seventh Day of July, 2015

Michelle K. Lee
*Director of the United States Patent and Trademark Office*